US008257966B2

(12) United States Patent
Hanafusa et al.

(10) Patent No.: US 8,257,966 B2
(45) Date of Patent: *Sep. 4, 2012

(54) REACTION KIT

(75) Inventors: Nobuhiro Hanafusa, Kyoto (JP); Koretsugu Ogata, Kyoto (JP); Koji Tanimizu, Kyoto (JP); Tomoichi Takahashi, Kyoto (JP); Atsushi Inami, Kyoto (JP); Ryuh Konoshita, Kyoto (JP); Masami Maekawa, Kyoto (JP); Takanori Mochizuki, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 619 days.

This patent is subject to a terminal disclaimer.

(21) Appl. No.: 12/279,840

(22) PCT Filed: Feb. 14, 2007

(86) PCT No.: PCT/JP2007/052567

§ 371 (c)(1), (2), (4) Date: Aug. 18, 2008

(87) PCT Pub. No.: WO2007/097229

PCT Pub. Date: Aug. 30, 2007

(65) Prior Publication Data

US 2010/0221816 A1 Sep. 2, 2010

(30) Foreign Application Priority Data

Feb. 20, 2006 (JP) ................................ 2006-043027
Apr. 17, 2006 (JP) ................................ 2006-112833
Jun. 1, 2006 (JP) ................................ 2006-153927
Jun. 1, 2006 (JP) ................................ 2006-153936

(51) Int. Cl.

| | |
|---|---|
| ***C12M 1/34*** | (2006.01) |
| ***B01L 3/00*** | (2006.01) |
| ***G01N 35/10*** | (2006.01) |
| ***G01N 1/28*** | (2006.01) |
| ***G01N 27/447*** | (2006.01) |

(52) U.S. Cl. ...... 435/287.2; 222/52; 204/600; 422/68.1; 422/401; 422/430

(58) Field of Classification Search ............... 435/287.2; 222/52; 204/600; 422/68.1, 401, 430
See application file for complete search history.

(56) References Cited

U.S. PATENT DOCUMENTS 4,808,453 A 2/1989 Romberg et al.
(Continued)

FOREIGN PATENT DOCUMENTS

JP 58-12859 U 1/1983
(Continued)

OTHER PUBLICATIONS

International Search Report for the Application No. PCT/JP2007/052567 mailed May 1, 2007.

*Primary Examiner* — Nathan Bowers
*Assistant Examiner* — Gautam Prakash
(74) *Attorney, Agent, or Firm* — Cheng Law Group, PLLC

(57) ABSTRACT

Disclosed is a reaction kit for preventing the entry of foreign matter into a reaction plate from the outside and the pollution of a surrounding environment. The reaction kit includes: a reaction plate (2) having, on the top surface side thereof, a reaction container (4) for carrying out the reaction of a sample and a reagent container (12) containing a reagent used for the reaction of a sample and sealed with a film (14); a dispensation tip (20) arranged on the top surface side of the reaction plate (2); a cover (24) covering a space above the top surface of the reaction plate (2) and movably supporting the dispensation tip (20) so that a distal end thereof is located inside the space covered with the cover (4) and a proximal end thereof is located outside the space; and a sample container (32) for introducing a sample into the space covered with the cover (24) from the outside through a sealable opening (31) provided in a part of the cover (24).

20 Claims, 23 Drawing Sheets

U.S. PATENT DOCUMENTS

| | | | | |
|---|---|---|---|---|
| 2003/0075557 | A1 | 4/2003 | Deppe et al. | |
| 2005/0106742 | A1 | 5/2005 | Wahl | |
| 2006/0029955 | A1 * | 2/2006 | Guia et al. | 435/6 |

FOREIGN PATENT DOCUMENTS

| | | | |
|---|---|---|---|
| JP | 64-070055 | A | 3/1989 |
| JP | 2001-121005 | A | 5/2001 |
| JP | 2003-070456 | A | 3/2003 |
| JP | 2003-511654 | A | 3/2003 |
| JP | 2003-532120 | A | 10/2003 |
| JP | 2005-130851 | A | 5/2005 |
| JP | 2005-214710 | A | 8/2005 |
| JP | 2005-291954 | A | 10/2005 |
| WO | WO-01/24933 | A1 | 4/2001 |

* cited by examiner

REACTION KIT

TECHNICAL FIELD

The present invention relates to a reaction kit suitable for carrying out various analyses such as biological analyses, biochemical analyses, and general chemical analyses in the fields of medical care, chemistry, and the like.

BACKGROUND ART

In biochemical analyses, general chemical analyses, and the like, micro multi-chamber devices are used as small-size reaction devices. As such a device, for example, a microwell reaction plate such as a microtiter plate, which has a flat plate substrate with a plurality of wells on the surface of the substrate, are used.

DISCLOSURE OF THE INVENTION

Problems to be Solved by the Invention

In the case of a conventional microwell reaction plate, the top surface of the reaction plate is exposed to ambient air during use. Therefore, there is a fear that foreign matter will enter a sample from the outside, and on the other hand, there is a possibility that a reaction product will pollute a surrounding environment.

It is therefore an object of the present invention to provide a reaction kit capable of preventing the entry of foreign matter from the outside into a reaction plate and the pollution of a surrounding environment.

Means for Solving the Problems

The present invention is directed to a reaction kit including: a reaction plate having a reaction container for carrying out the reaction of a sample on the top surface side thereof; a dispensation tip arranged above the top surface of the reaction plate; and a cover covering a space above the top surface of the reaction plate and movably supporting the dispensation tip so that a distal end thereof is located inside the space covered with the cover and a proximal end thereof is located outside the space covered with the cover.

In the case of using such a reaction kit, it is necessary to introduce a sample into the space covered with the cover in one way or another, but a method for introducing a sample into the space is not particularly limited. For example, the reaction kit may further include a sample introduction unit for introducing a sample into the space from the outside through a sealable opening provided in a part of the cover.

The sample introduction unit may have a sealing member adhered to the cover after a sample is introduced into the space so as to hermetically seal the opening.

In a case where a sample is introduced into the space from the outside through a sample introduction port and then the sample introduction port is hermetically sealed, it is necessary to open a cap of the sample introduction port at least once. However, in this case, there is a fear that foreign matter will enter the sample from the outside during the time interval from opening the cap to dispense the sample to closing the cap. In addition, opening and closing of the cap of the sample introduction port is troublesome. For this reason, the sample introduction port may comprise an elastic member through which a sharp-tipped dispensation tool can pass to form a through hole closable by pulling out the dispensation tool due to its elasticity. Further, a sealing film may be adhered to the sample introduction port to hermetically seal the sample introduction port. Thus, it is possible to prevent the leakage of a sample attached to the elastic member into an outside environment and thus to prevent the pollution of an outside environment with the sample.

A preferred example of the sample introduction unit is a container having a sample introduction port provided in the side surface thereof and an opening provided in the upper part thereof. The container may previously contain a sample pretreatment solution or a reagent.

Further, the opening of the container may be sealed with a cover film adhered thereto. By dosing so, it is possible to prevent a sample contained in the container from being dried or to prevent a sample from spilling over the container even when the reaction kit is dropped by mistake.

It is also necessary to introduce a reagent used for the reaction of a sample into the space covered with the cover in one way or another, but a method for introducing a reagent into the space is not particularly limited either. For example, a reagent may be introduced into the space together with a sample through the sample introduction unit, or a reagent may be introduced into the space by using another container, or a reagent may be previously contained in the reaction plate. In a case where a reagent is previously contained in the reaction plate, the reagent is contained in a reagent container provided on the top surface side of the reaction plate and sealed with a film. The film for covering and sealing the reagent container is one through which the dispensation tip can pass.

As described above, since a space above the top surface of the reaction plate is covered with the cover cut off from the outside, the reaction of a sample is carried out in the space. Further, detection of a reaction product obtained by the reaction is also carried out in the space covered with the cover without transferring the reaction product to the outside of the cover. After the completion of the detection, the reaction kit is disposed of with the reaction product remaining in the space covered with the cover. That is, the reaction kit according to the present invention is disposable.

The dispensation tip may be one which is attached to the tip of a dispensation nozzle. However, in this case, it is necessary to separately provide a nozzle mechanism for carrying out dispensation operation. Therefore, in order to eliminate the necessity to provide a nozzle mechanism, the dispensation tip of the reaction kit according to the present invention preferably has a syringe driven from the outside of the cover. In this case, it is possible to carry out dispensation operation by driving the syringe. Further, in this case, the syringe seals the passage of the dispensation tip, and therefore it is possible to prevent the space covered with the cover and the outside of the cover from intercommunicating with each other through the passage of the dispensation tip.

In a case where the dispensation tip does not have a syringe, the space covered with the cover can be sealed with the nozzle mechanism during dispensation operation, but intercommunicates with the outside of the cover through the dispensation tip during the time when the dispensation tip is not used, for example, during reaction or detection. Therefore, in order to prevent the entry of foreign matter from the outside into the reaction kit and the leakage of a sample and a reaction product into the outside even when the dispensation tip does not have a syringe, the dispensation tip preferably has a filter in the tip portion thereof.

In a case where the reaction kit is intended for use in gene analysis, the reaction plate preferably has a gene amplification unit for carrying out gene amplification reaction. The gene amplification unit is preferably formed to have a shape suitable for temperature control carried out according to a predetermined temperature cycle. Such a gene amplification unit can be achieved by allowing the reaction container to have such a shape or by providing a container for gene amplification reaction separately from the reaction container. Examples of the gene amplification reaction include PCR and LAMP.

A reaction product formed in the reaction container can be analyzed in the reaction container. Alternatively, the reaction product may be transferred from the reaction container to another portion on the reaction plate to carry out analysis. In a case where the reaction kit is designed to allow a reaction product to be analyzed in the reaction container, the reaction container is preferably made of an optically-transparent material so that a reaction product can be optically analyzed from the bottom side of the reaction container.

On the other hand, in a case where the reaction kit is designed to allow a reaction product to be transferred from the reaction container to another portion for carrying out analysis, the reaction plate further includes an analysis unit provided on the top surface side thereof to analyze a reaction product formed in the reaction container.

As one example of the analysis unit, an electrophoresis unit for analyzing a reaction product by electrophoretic separation can be mentioned. When a reaction product contains a gene, a probe region where probes reacted with the gene are arranged is used as another example of the analysis unit. Examples of such a probe region include DNA chips and hybridization regions.

An example of a structure for holding and movably supporting the dispensation tip includes one which is formed of an airtight and flexible material and is capable of holding and movably supporting the dispensation tip, such as a diaphragm or a film. In this case, the cover may have a cover main body having stiffness and provided integrally with the reaction plate and an upper cover attached to the cover main body so as to be arranged above the top surface of the reaction plate and have a diaphragm or a film which is formed of an airtight and flexible material and is capable of holding and movably supporting the dispensation tip. Further, in this case, an opening, in which the sample introduction unit is arranged, is provided in the cover main body, and the sealing member for hermetically sealing the opening is adhered to the cover main body.

In order to smoothly move the dispensation tip, a movable portion of the cover may be formed of a flexible material of which, at least, the outer surface has been subjected to surface treatment to reduce a coefficient of friction to prevent a frictional load from being applied to the movable portion.

The surface treatment for the cover is required to provide a smooth surface capable of responding to the movement of a cover drive unit and to reduce a coefficient of friction to prevent a frictional load from being applied to the movable portion of the cover. An example of such surface treatment includes polyparaxylylene resin coating. The polyparaxylylene resin coating can be carried out by, for example. ® PARYLENE COATING which is a method for chemical vapor deposition (CVD) coating using a polyparaxylylene resin.

As another example of the surface treatment for the cover, fluorocarbon resin coating may also be used. The fluorocarbon resin coating can be carried out using, for example, ® NOVEC EGC-1720 as a fluorine-based surface treating agent. The fluorine-based surface treating agent is a solution obtained by dissolving a fluorocarbon resin in a solvent. In this case, the fluorine-based surface treating agent is applied onto an object to be surface-treated by dipping the object in the solution (i.e., by dip coating) or by brushing the solution on the object or by spin coating, and then dried at room temperature or by heating to 60 to 120° C. In this way, the object is coated with the fluorine-based surface treating agent.

Further, the cover is required to have gas impermeability, and therefore a flexible material constituting the cover is preferably one that can be formed into a membrane such as a diaphragm or a thin film. Preferred examples of such a material include silicone rubber, ethylene propylene rubber (EPDM), and butyl rubber.

Another example of the structure for holding and movably supporting the dispensation tip includes a cover including a cover main body provided integrally with the reaction plate and a cover plate arranged above the top surface of the reaction plate and held by the cover main body by means of a sealing material so as to be able to slide in a horizontal surface while the space covered with the cover is kept hermetically sealed. In this case, the dispensation tip is supported by the cover plate by means of another sealing material so as to be able to slide in the vertical direction while the space covered with the cover is kept hermetically sealed, and an opening in which the sample introduction unit is arranged is provided in the cover main body and the sealing member for hermetically sealing the opening is adhered to the cover main body.

The reaction kit according to the present invention is intended for use in measuring various reactions such as chemical reactions and biochemical reactions.

Examples of a sample measured using the reaction kit according to the present invention include, but are not limited to, chemical substances, biological samples, living body-derived sample, and the like.

Effect of the Invention

The reaction kit according to the present invention is used with a space above the top surface of the reaction plate being covered with the cover, and therefore it is possible to prevent the entry of foreign matter from the outside into a sample and the pollution of an outside environment with a reaction product.

By allowing the reaction kit to further include a sample introduction unit, it is easy to introduce a sample into the space covered with the cover.

When the sample introduction unit has a sealing member adhered to the cover to hermetically seal an opening provided in a part of the cover after a sample is introduced into the space covered with the cover through the sample introduction unit, the opening can be completely sealed hermetically by adhering the sealing member to the cover after the sample is introduced into the space from the outside through the opening of the sample introduction unit. Further, as described above, since the reaction kit according to the present invention is used with a space above the top surface of the reaction plate being covered with the cover, it is possible to prevent both the entry of foreign matter from the outside into a sample and the pollution of an outside environment with a reaction product.

When the reaction kit according to the present invention further includes a sample introduction unit for introducing a sample into the space covered with the cover from the outside through a sealable sample introduction port provided in a part of the cover, the reaction kit can be used with a space above the top surface of the reaction plate being covered with the cover and the sample introduction port can be formed from an elastic member through which a sharp-tipped dispensation tool can pass to form a through hole closable by pulling out the dispensation tool due to its elasticity, and therefore it is possible to prevent both the entry of foreign matter from the outside into a sample and the pollution of an outside environment with a reaction product. In addition, it is also possible to easily hermetically seal the sample introduction port and to prevent a sample from being dried even when the amount of the sample is very small. This makes it possible to analyze a reaction product accurately.

In a case where the sample introduction unit is provided as a container having a sample introduction port provided in the side surface thereof and an opening provided in the upper part thereof to storage a liquid, it is possible to easily carry out introduction and dispensation of a sample.

By adhering a cover film to the opening provided in the upper part of the sample introduction unit, it is possible to prevent a liquid from being dried in the reaction kit and to prevent another reagent from being contaminated with the liquid. This makes it possible to analyze a reaction product accurately.

By adhering a sealing film to the sample introduction port, it is possible to prevent the leakage outside of a sample attached to the elastic member and thus to prevent the pollution of an outside environment with the sample.

By allowing both a sample and a reagent for use in the reaction of the sample to be introduced into the reaction kit through the sample introduction unit, it is possible to expand the versatility of the reaction kit. On the other hand, by allowing the reagent to be previously contained in the reaction plate, it is possible to eliminate the necessity to prepare the reagent in equipment for treating the reaction kit, thereby simplifying the reaction kit treatment equipment.

By allowing the dispensation tip to have a syringe operated from the outside of the cover, it is possible to eliminate the necessity to separately provide a nozzle mechanism.

By allowing the reaction plate to further have a gene amplification unit, it is possible to amplify a gene by gene amplification reaction such as PCR or LAMP even when a sample contains only a very small amount of gene as a measurement object, thereby enhancing analytical accuracy.

Even when the dispensation tip does not have a syringe, by allowing the dispensation tip to have a filter in the tip portion thereof, it is possible to prevent the entry of foreign matter from the outside through the dispensation tip and to prevent the leakage of a reaction product into the outside through the dispensation tip and thus to prevent the pollution of an outside environment with the reaction product.

In a case where gene amplification reaction is carried out, in general, there is a problem in which other DNA will enter a sample from the outside. In addition, there is also a problem in which other samples will be contaminated with an amplified gene. However, the reaction kit according to the present invention allows gene amplification reaction to be carried out in an enclosed space, and therefore it is possible to prevent a sample from being contaminated with other DNA entering from outside. Further, the reaction kit according to the present invention is disposed of with a reaction product being trapped in the enclosed space after the completion of analysis, and therefore it is possible to eliminate the fear that other samples will be contaminated with an amplified gene.

By allowing a reaction product formed in the reaction container to be analyzed in the reaction container, an electrophoresis unit provided separately from the reaction container, or a probe region where probes to be reacted with a gene are arranged, it is possible to expand the choice of samples which can be treated by the reaction kit according to the present invention.

A structure for holding and movably supporting the dispensation tip can easily be achieved by using an airtight and flexible material or by constituting the cover from a cover main body and a cover plate supporting the dispensation tip so that the dispensation tip can be moved by sliding the cover plate supported by the cover main body and by sliding it supported by the cover plate.

By forming the cover using a flexible material having been subjected to surface treatment to reduce a coefficient of friction, it is possible to reduce the coefficient of friction of the surface of the cover, and therefore to smoothly move the dispensation tip, thereby reducing a frictional load applied to a drive unit and thus preventing the occurrence of a problem that the cover is broken.

The polyparaxylylene resin coating as one example of the surface treatment is more preferred because it has the effect of reducing not only the coefficient of friction of the surface of the cover but also gas permeation.

The fluorocarbon resin coating as another example of the surface treatment has the effect of reducing the coefficient of friction of the surface of the cover.

By allowing the reaction kit according to the present invention to further include a sample introduction unit, it is possible to easily introduce a sample into the space covered with the cover.

DESCRIPTION OF THE REFERENCE NUMERALS

Figure 1A:
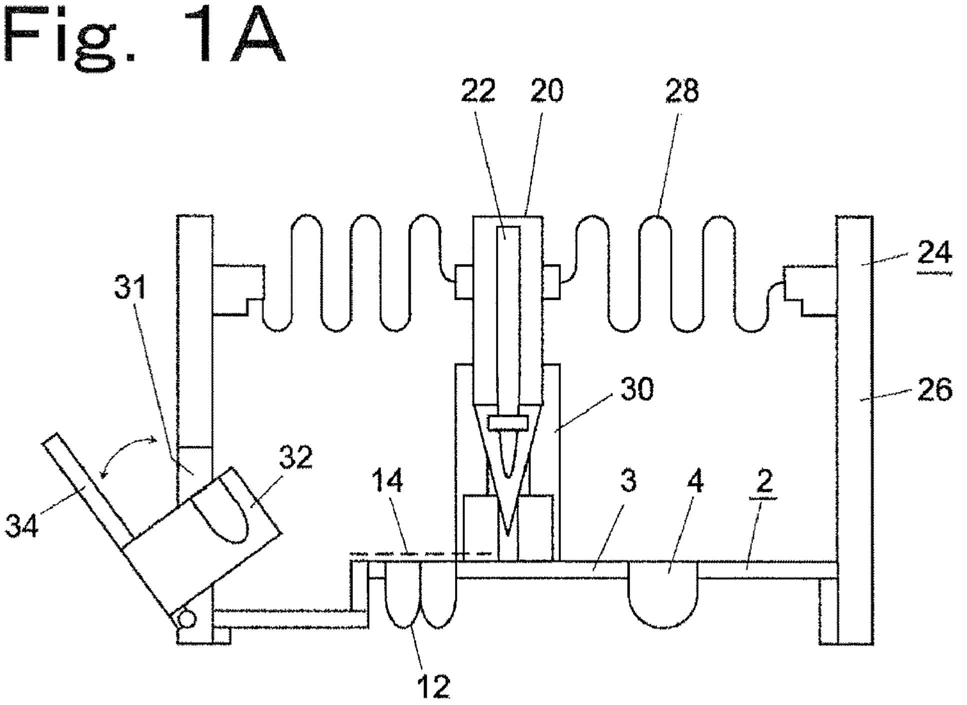
FIG. 1A is a vertical sectional view of one example of a reaction kit.

2, 2*a*, 2*b*, 2*c* reaction plate
3 substrate
4 reaction container
12 reagent container
14, 14*a*, 14*b* film
20 dispensation nozzle
20*b* dispensation tip of a dispensation tool
22 plunger of syringe
23 filter
24 cover
26 cover main body
28 bellows film
32, 32*a* sample container
32*b* sample introduction unit
33*b* sample introduction port
33*c* elastic member
35 sealing member
64, 64*a*, 71 cover plate
66, 68, 72 sealant
100, 110, 120 DNA chip
106 electrode
102 electrophoretic separation channel

BEST MODE FOR CARRYING OUT THE INVENTION

Figure 1B:
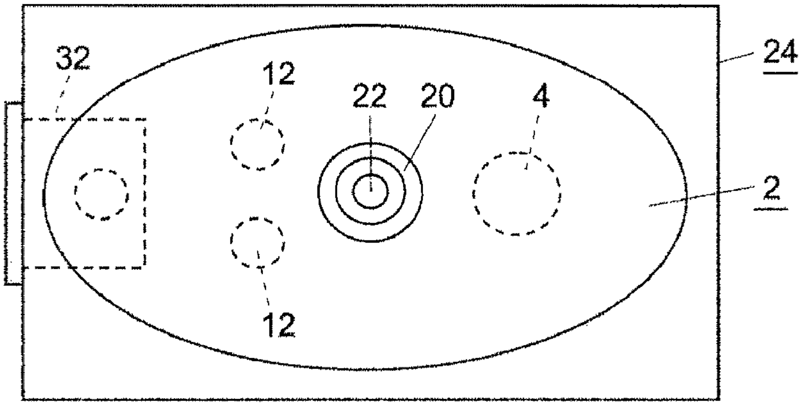
FIG. 1B is a plan view showing a reaction plate and a dispensation tip of the reaction kit.
Figure 1C:
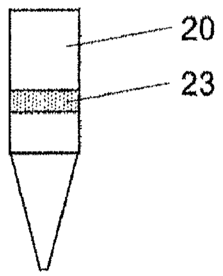
FIG. 1C is a sectional view schematically showing another example of the dispensation tip.
Figure 2:
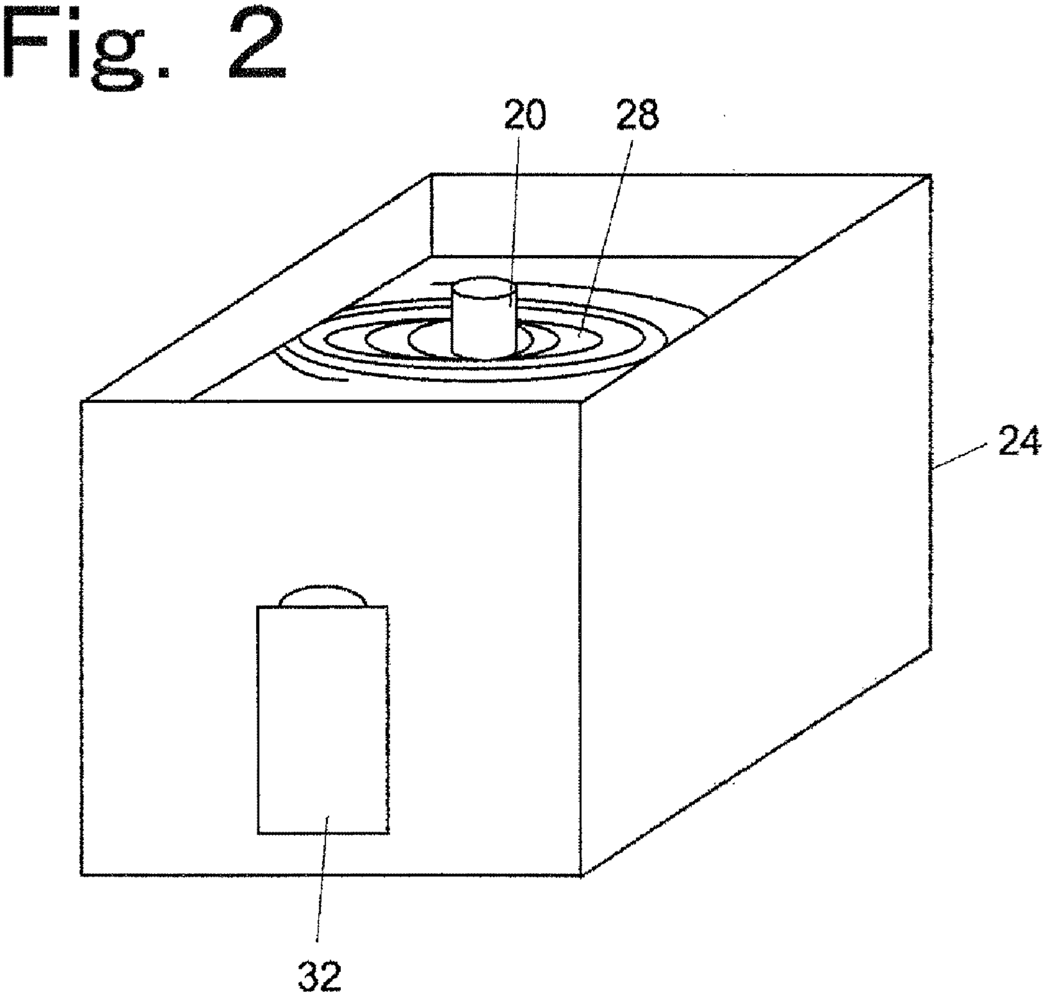
FIG. 2 is a perspective view showing the appearance of the same reaction kit as in FIG. 1A.

FIGS. 1A-1C show one example of a reaction kit, of which FIG. 1A is a vertical sectional view of the reaction kit, FIG. 1B is a plan view showing a reaction plate and a dispensation tip 20 of the reaction kit, FIG. 1C is a sectional view schematically showing another example of the dispensation tip, and FIG. 2 is a perspective view of the reaction kit.

As shown in FIGS. 1A and 1B, the reaction plate 2 has a reaction container 4 for carrying out reaction of a sample and reagent containers 12 for receiving reagents used for the reaction of the sample on the top surface of a substrate 3. Each of the reagent containers 12 is sealed with a film 14.

The reaction container 4 is provided as a recess in the top surface of the substrate 3. In a case where the reaction container 4 is intended for reaction carried out under externally-controlled temperature conditions, a part of the reaction container 4 subjected to temperature control preferably has a small thickness to enhance heat conductivity.

Each of the reagent containers 12 is also provided as a recess in the top surface of the substrate 3, and contains a reagent to be used for reaction, and is covered with the film 14 through which the dispensation tip 20 (which will be described later) can pass. Examples of such a film 14 include an aluminum foil and a laminated film having an aluminum film and a resin film such as a PET (polyethylene terephthalate) film. The film 14 is attached by welding or adhesion so as not to be easily detached.

If necessary, a mixing chamber for mixing a sample with a reagent may be provided as a recess in the top surface of the substrate 3. Further, such a mixing chamber may be covered with the film 14 with its recess being empty.

The reaction container 4 may be used as a detection chamber for detecting a reaction product formed in the reaction container 4. In this case, detection of a reaction product can be carried out by, for example, means for externally irradiating the reaction container 4 with light. Alternatively, a detection chamber may be provided separately from the reaction container 4. For example, in a case where a plurality of detection chambers are provided separately from the reaction container 4, the detection chambers may previously contain different reagents for detecting the state of a reaction mixture obtained by the reaction of a sample with a reagent, and the reaction mixture is dispensed into the detection chambers by the dispensation tip 20. The opening of such a detection chamber may be covered with a film through which the dispensation tip 20 can pass. As in the case of the film 14, examples of the film for covering the detection chamber include an aluminum foil and a laminated film having an aluminum film and a resin film such as a PET film, and the film can be attached by welding or adhesion so as not to be easily detached.

The material of the substrate 3 having the reaction container 4 is not particularly limited, but is preferably cheaply available because the reaction kit is disposable. Preferred examples of such a material include resin materials such as polypropylene and polycarbonate. In a case where the reaction kit is designed to allow a reaction product to be detected by absorbance, fluorescence, chemiluminescence, or bioluminescence in the reaction container 4 or a detection chamber provided separately from the reaction container 4, the substrate 3 is preferably made of an optically-transparent resin so that the reaction product can be optically detected from the bottom surface side of the substrate 3. Particularly, in a case where a reaction product is detected by fluorescence, the substrate 3 is preferably made of a low self-fluorescence (i.e., the amount of fluorescence emitted from a material itself is small) and an optically-transparent resin such as polycarbonate. The thickness of the substrate 2 is in the range of 0.3 to 4 mm, preferably in the range of 1 to 2 mm. From the viewpoint of low self-fluorescence, the thickness of the substrate 3 is preferably small.

The dispensation tip 20 is arranged above the top surface of the reaction plate 2. The dispensation tip 20 is used to dispense a sample and a reagent. Further, in a case where the reaction plate 2 has a detection chamber provided separately from the reaction container 4, the dispensation tip 20 is used also to dispense a reaction mixture obtained by reacting a sample with a reagent into the detection chamber. The dispensation tip 20 has a syringe 22, and the syringe 22 is driven from the outside of a cover 24 to carry out dispensation operation.

As shown in FIG. 1C, the dispensation tip 20 may have a filter 23 in its inside instead of the syringe 22. The filter adsorbs foreign matter entering from the outside, and is therefore more effective to prevent the entry of foreign matter into a space covered with the cover 24 and to prevent the release of reactants and a reaction product from the space covered with the cover 24 into the outside.

The cover 24 is provided so as to cover a space above me top surface or tne reaction plate 2. The cover 24 includes a cover main body 26 for covering the periphery of the reaction plate 2 and a bellows film (movable portion) 28 for covering the top of the reaction plate 2 so that a space above the top surface of the reaction plate 2 is cut off from the outside. The cover main body 26 is provided integrally with the reaction plate 2 by fixing the lower end of the cover main body 26 to the reaction plate 2 or by using a sealant provided between the lower end of the cover main body 26 and the reaction plate 2, and has stiffness to maintain the shape of the cover 24. The bellows film 28 is formed from a flexible diaphragm or a flexible film, and movably holds the dispensation tip 20 so that a distal end thereof is located inside a space covered with the cover 24 and a proximal end thereof is located outside the space covered with the cover 24.

The material of the cover 24 is not particularly limited as long as it can cover a space above the top surface of the reaction plate 2 while keeping the reaction kit hermetically sealed. However, the cover 24 is preferably made of a cheaply-available material because the reaction kit is disposable. Preferred examples of a material for forming the cover main body 26 include resin materials such as polypropylene and polycarbonate, and preferred examples of a material for forming the bellows film 28 include nylon, polyvinyl chloride, and rubber materials such as silicone rubber and the like.

A holding member 30 for holding the dispensation tip 20 before and after its use is provided on the cover main body 26 or the substrate 3. When used for dispensation operation, the dispensation tip 20 is detached from the holding member 30 so as to be freely moved over the top surface of the reaction plate 2.

The cover main body 26 has an opening 31 for supplying a sample onto the reaction plate 2 from the outside of the cover 24. Further, a sample container 32 is openably and closably attached to the opening 31. The sample container 32 has a recess for receiving a sample, and the recess has an opening formed in the top surface of the sample container 32. After a sample is injected into the recess and is then placed inside the cover 24, the opening 31 is hermetically sealed by bringing a plate 34 holding the sample container 32 into intimate contact with the cover main body 26 using a pressure-sensitive adhesive applied onto the inner surface of the plate 34 or by engaging the plate 34 with the cover main body 26 with a sealant interposed therebetween. That is, the opening 31 is an opening hermetically sealable.

The reaction kit is disposable, and is therefore entirely disposed of without removing the cover 24 from the reaction plate 2 after the completion of analysis of one sample.

Hereinafter, the operation of analyzing a sample with the reaction kit will be described.

Prior to analysis, a sample is injected into the sample container 32 through the opening 31, and then the opening 31 is closed by the sample container 32, and therefore the sample container 32 is fixed to the cover main body 26. As a result, the sample is placed in a space covered with the cover 24 of the reaction kit and is cut off from the outside.

Figure 3:
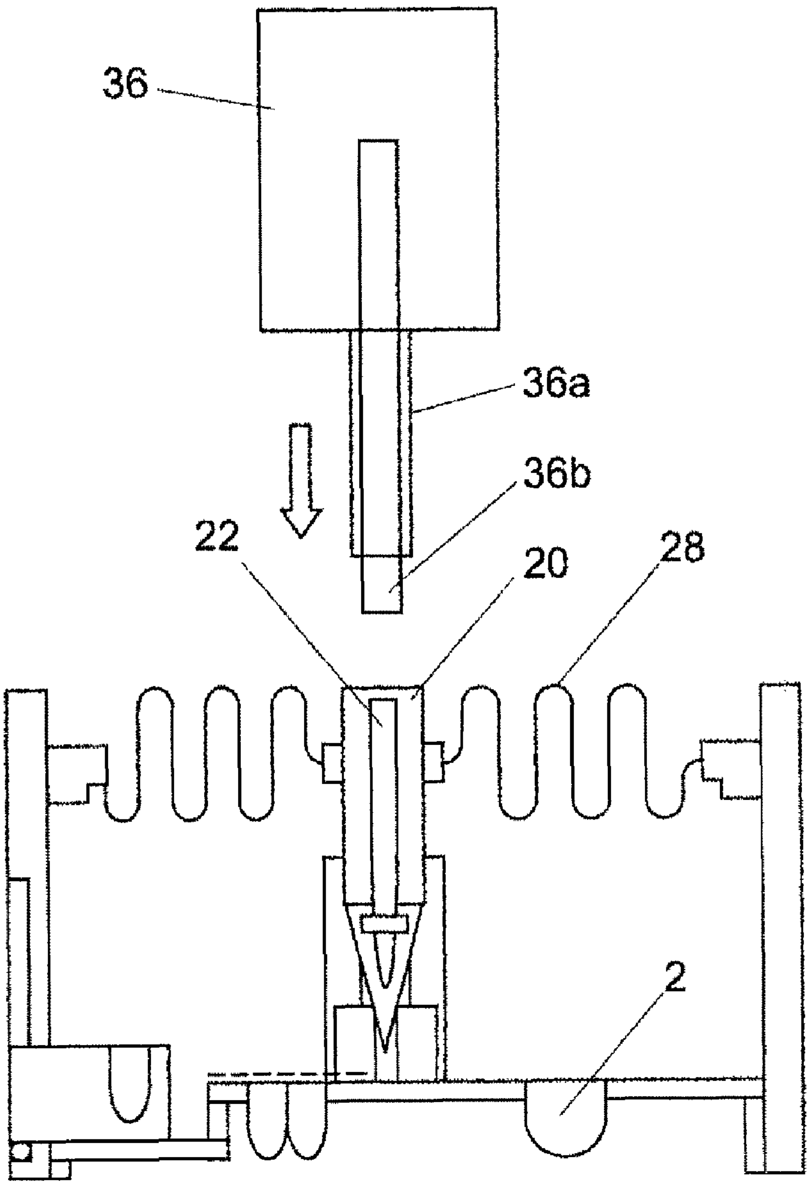
FIG. 3 is a vertical sectional view showing a state after a sample is introduced into the reaction kit.

After the sample is introduced into the reaction kit, as shown in FIG. 3, engagement of a drive unit 36 with the dispensation tip 20 and the syringe 22 is allowed to start.

Figure 4:
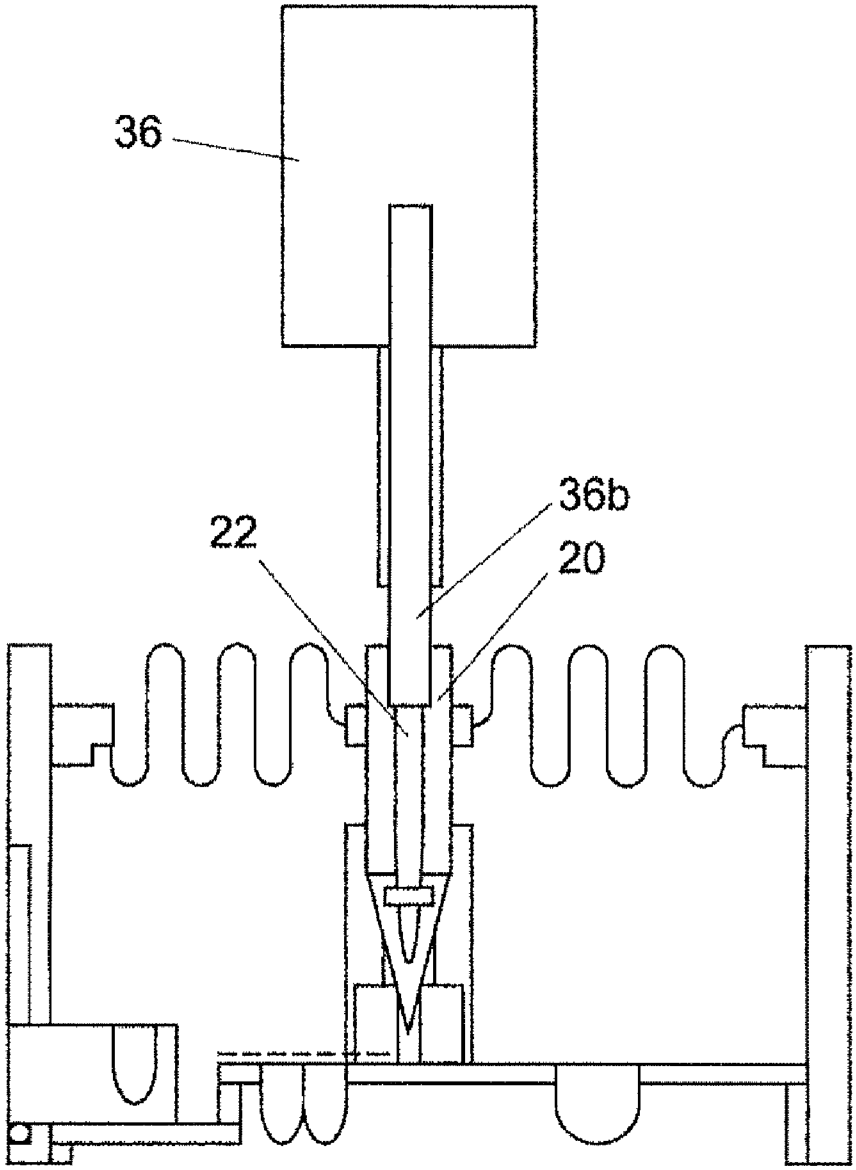
FIG. 4 is a vertical sectional view showing a state after a syringe drive section of a drive unit is engaged with a plunger of a syringe in the reaction kit.

First, as shown in FIG. 4, a plunger holder **36*b* as a syringe drive section is moved down to be engaged with a plunger of the syringe 22**.

Figure 5:
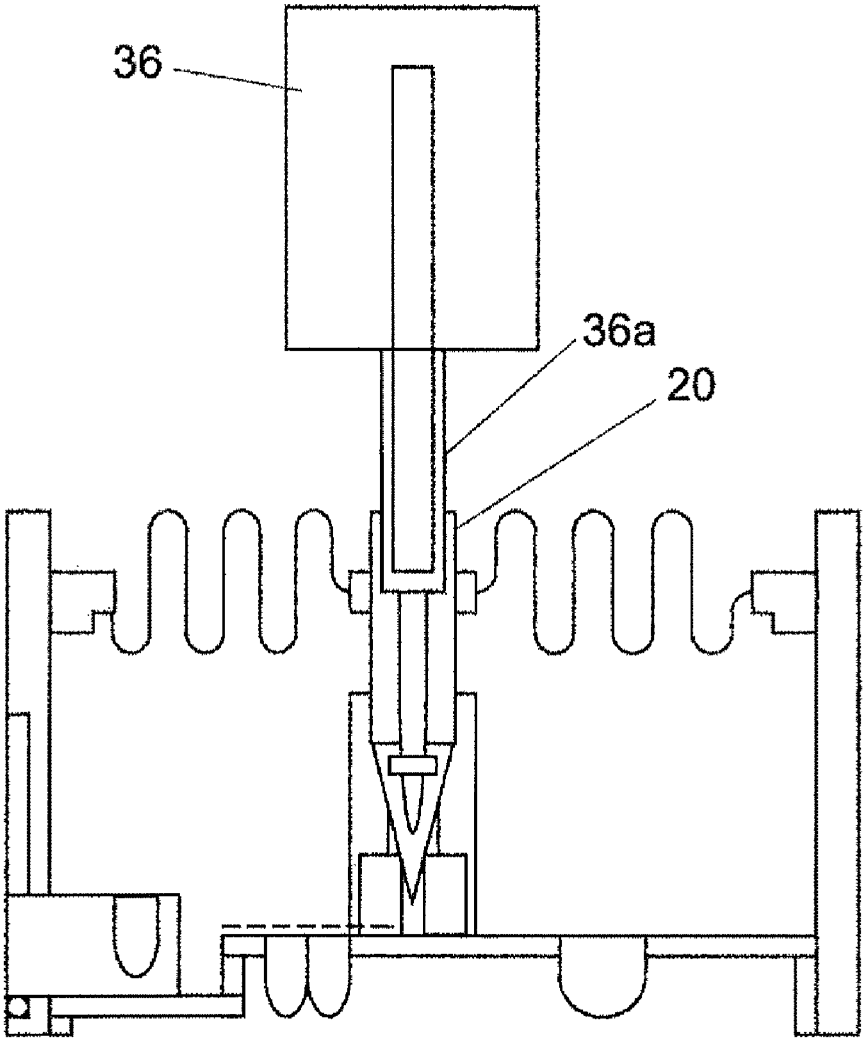
FIG. 5 is a vertical sectional view showing a state after a tip holding section of the drive unit is engaged with the dispensation tip in the reaction kit.

Then, as shown in FIG. 5, a tip holder **36*a* is also moved down to be press-fitted to the dispensation tip 20 so that the dispensation tip 20 is held by the tip holder 36*a***.

Figure 6:
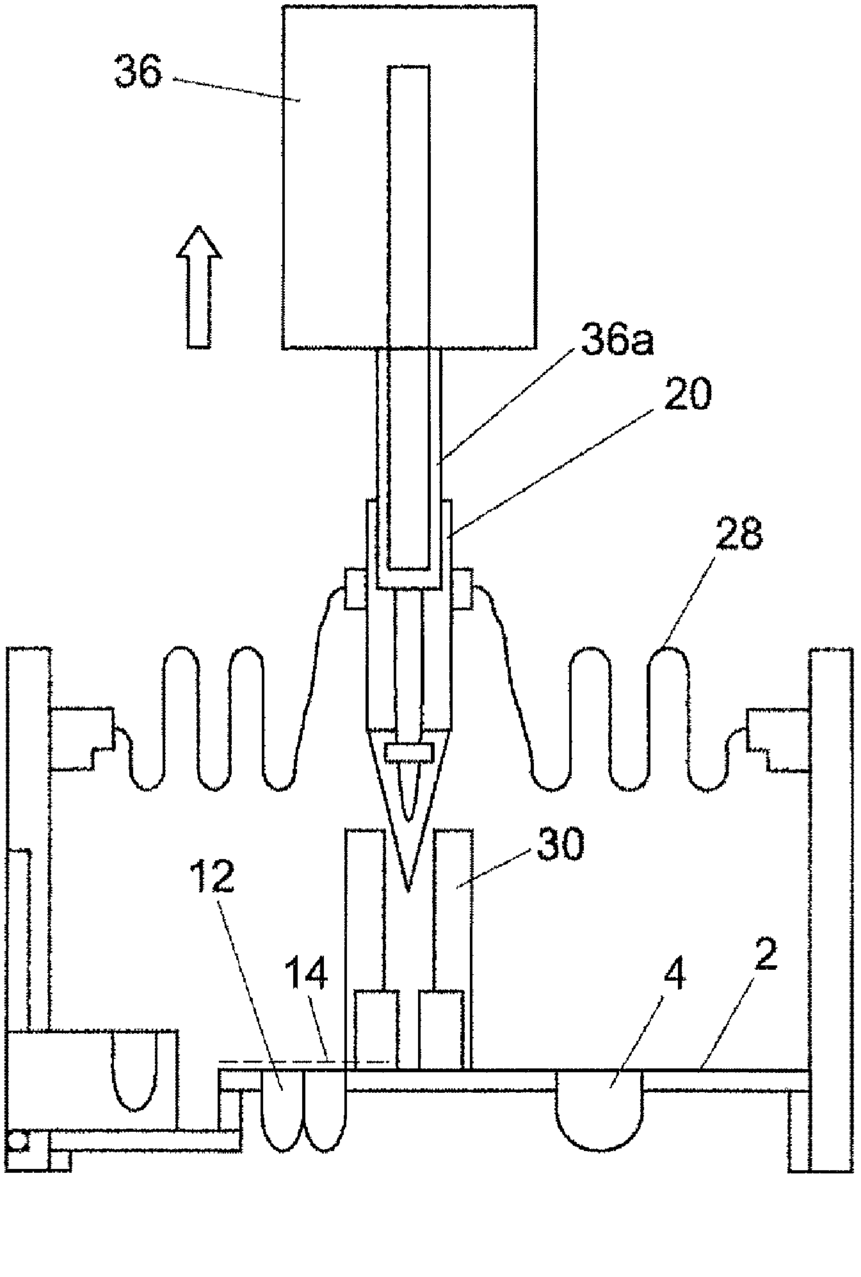
FIG. 6 is a vertical sectional view showing a state after the dispensation tip is detached from the holding section in the reaction kit.

Next, as shown in FIG. 6, the dispensation tip 20 is detached from the holding section 30. In this way, the dispensation tip 20 becomes able to be freely moved by the bellows film 28 with its distal end being cut off from the outside.

The dispensation tip 20 is moved to the sample container 32 to take a sample, and then the sample is dispensed into the reaction container 4 by the dispensation tip 20.

Then, the dispensation tip 20 is moved to the reagent container 12, and the distal end of the dispensation tip 20 is passed through the film 14 to take a reagent from the reagent container 12, and the reagent is dispensed into the reaction container 4 by the dispensation tip 20 to react the sample with the reagent. If necessary, the reaction container 4 is brought into contact with an external heat source during the reaction to adjust the temperature of the reaction container 4 to a predetermined temperature.

During or after the reaction, detection of a reaction product is carried out. In this case, it is assumed that a reaction product contained in the reaction container 4 is optically detected from the outside of the reaction plate 2. Therefore, a detection unit is arranged below the reaction container 4 to detect a reaction product by optical means or other means.

As described above example, the reaction plate 2 has reagent containers 12, but the reagent containers 12 can be omitted from the reaction plate 2. In this case, both a sample and a reagent may be injected into the sample container 32 to introduce them into the reaction kit, or another container not shown may be used to introduce a reagent into the reaction kit.

Figure 7:
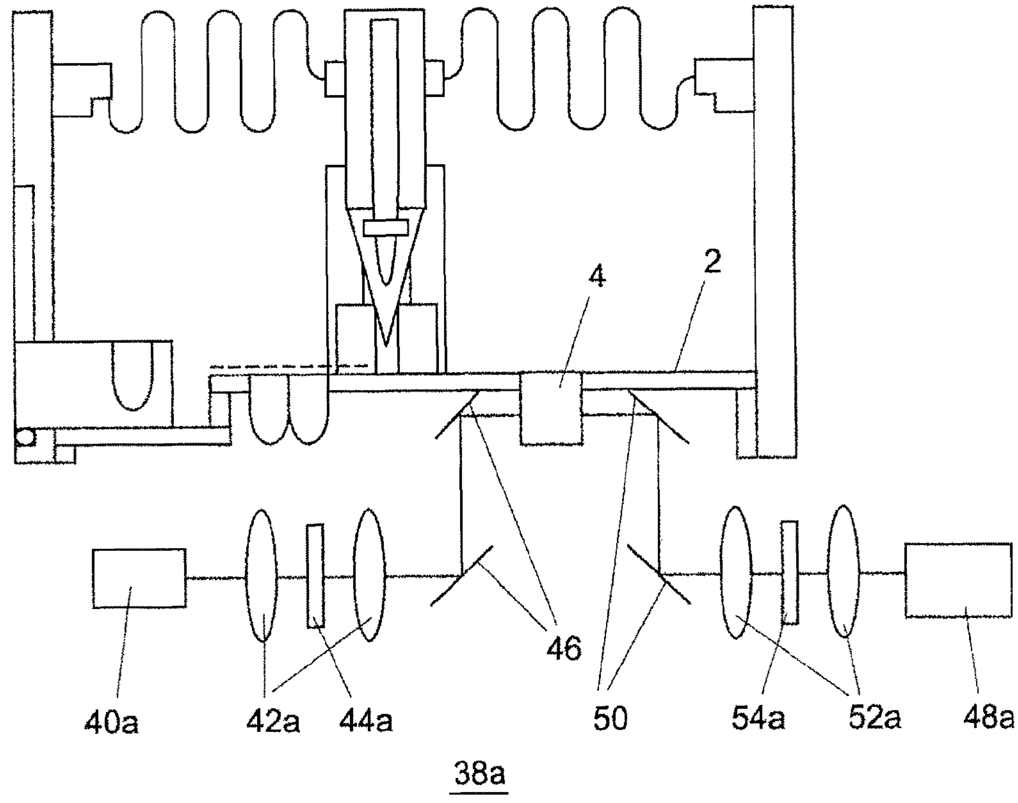
FIG. 7 is a vertical sectional view showing a first example of a detection unit used for the detection of a reaction product in the reaction kit treatment equipment according to the present invention.
Figure 8:
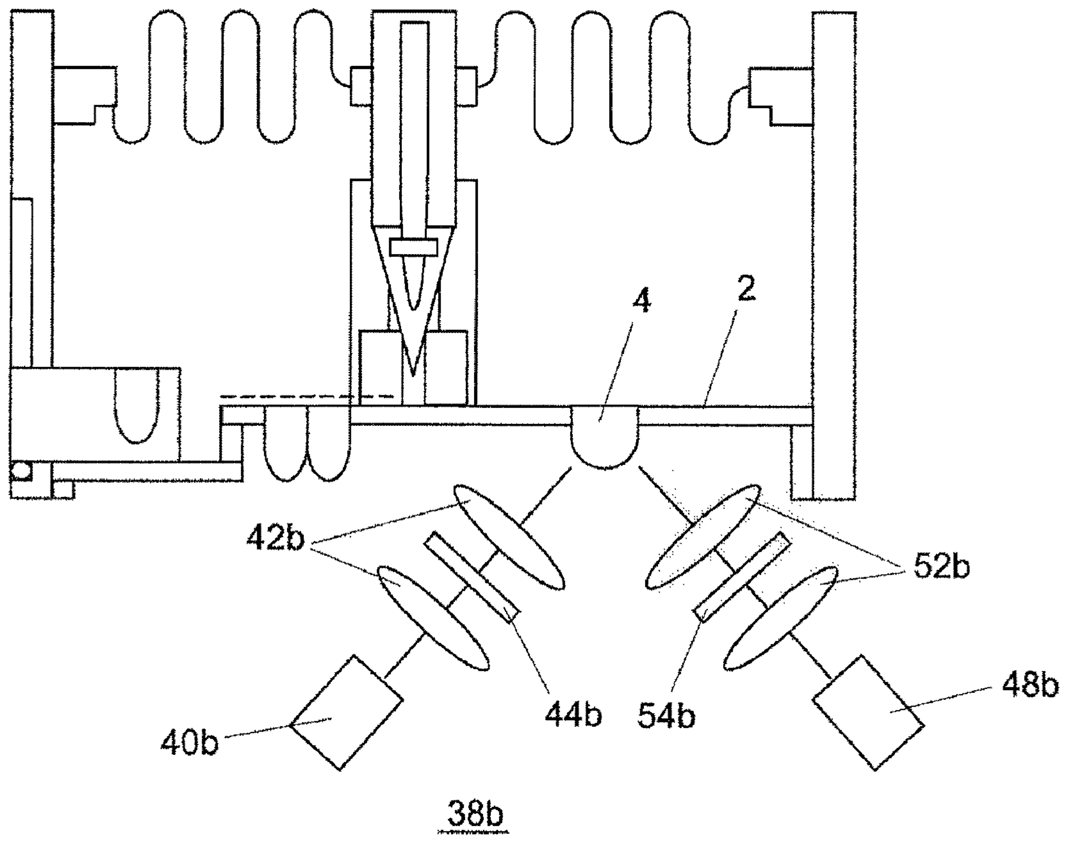
FIG. 8 is a vertical sectional view showing a second example of the detection unit used for the detection of a reaction product in the reaction kit treatment equipment according to the present invention.
Figure 9:
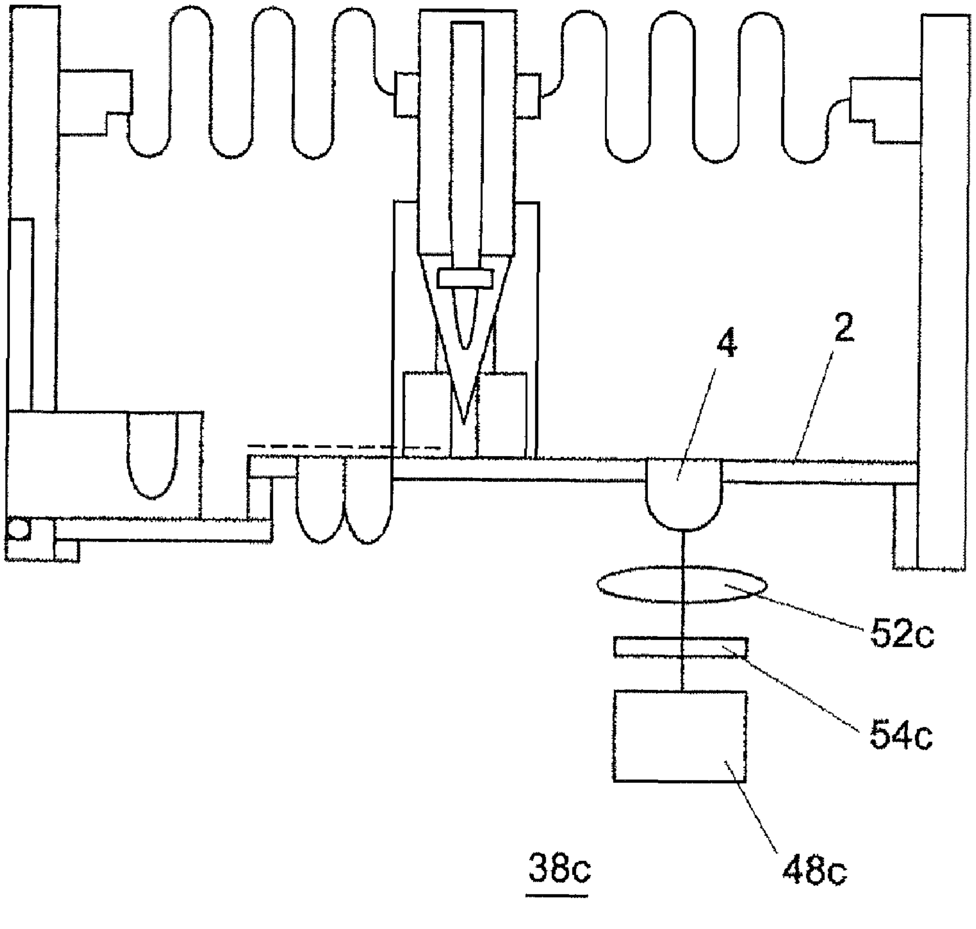
FIG. 9 is a vertical sectional view showing a third example of the detection unit used for the detection of a reaction product in the reaction kit treatment equipment according to the present invention.

FIGS. 7 to 9 show examples of a detection unit used to detect a reaction product in the reaction container of the reaction kit according to the present invention.

FIG. 7 shows an example of the detection unit including an absorbance detector. In this case, the reaction container 4 preferably has a pair of parallel flat surfaces serving as a light incident surface through which measuring light enters and a light exiting surface through which measuring light exits.

A detection unit 38*a* includes an irradiation optical system. The irradiation optical system has, on its optical path, a light source 40*a*, a pair of lenses 42*a* for once condensing light emitted from the light source 40*a* to obtain parallel light and then condensing the parallel light to irradiate the reaction container 4 with condensed light, a filter 44*a* arranged between the pair of lenses 42*a* at a position where the parallel light travels to select light having a predetermined wavelength from light emitted from the light source 40*a* to obtain measuring light, and mirrors 46 for guiding the measuring light to the light incident surface of the reaction container 4. As the light source 40*a*, a lamp light source such as a tungsten lamp which emits light having wavelengths ranging from the ultraviolet light region to the visible light region, a light-emitting diode (LED), a laser diode (LD), or the like is used. Further, the detection unit 38*a* includes a light-receiving optical system. The light-receiving optical system has, on its optical path, a photodetector 48*a*, mirrors 50 for guiding light exiting from the reaction container 4 through its light exiting surface to the photodetector 48*a*, a pair of lenses 52 for once converting the light into parallel light and then condensing the parallel light to introduce condensed light into the photodetector 48*a*, and a filter 54*a* arranged between the pair of lenses 52 at a portion where the parallel light travels to select light having a predetermined wavelength suitable for measurement.

The reason for once converting light into parallel light by the lenses 42*a* and 52*a* is to improve the precision of wavelength selection by the filters 44*a* and 54*a*.

In the case of using such a detection unit 38*a*, light having a wavelength suitable for detecting a reaction product is selected from light emitted from the light source 40*a* by the filters 44*a* and 54*a*, and absorbance is measured at the selected wavelength to detect the reaction product.

FIG. 8 shows an example of a detection unit including a fluorescence detector.

A detection unit 38*b* includes an excitation optical system. The excitation optical system has a light source 40*b*, a pair of lenses 42*b* for once condensing light emitted from the light source 40*b* to obtain parallel light and then condensing the parallel light to irradiate the reaction container 4 with condensed light, and a filter 44*b* arranged on the optical path of parallel light beams obtained by the lens 42*b* to select light having a predetermined excitation wavelength from light emitted from the light source 40*b*. Further, the detection unit 38*b* includes a light-receiving optical system. The light-receiving optical system has a photodetector 48*b*, a pair of lenses 52*b* for receiving fluorescence emitted from the reaction container 4, once converting the fluorescence into parallel light, and condensing the parallel light to introduce condensed light into the photodetector 48*b*, and a filter 54*b* arranged on the optical path of the parallel fluorescence beams obtained by the lens 52*b* to select light having a predetermined fluorescence wavelength. Similarly, the reason for once converting light into parallel light by the lenses 42*b* and 52*b* is to improve the precision of wavelength selection by the filters 44*b* and 54*b*.

In the case of using such a detection unit 38*b*, light having an excitation wavelength for exciting a reaction product is selected from light emitted from the light source 40*b* by the filter 44*b* to irradiate the reaction product contained in the reaction container 4 with the selected light, and fluorescence emitted from the reaction product is received by the light-receiving optical system, and light having a predetermined fluorescence wavelength is selected by the filter 54*b*, and the selected fluorescence is detected by the photodetector 48*b*.

FIG. 9 shows an example of the detection unit for detecting chemiluminescence or bioluminescence emitted from a reaction product.

A detection unit 38*c* has a photodetector 48*c* for detecting light emitted from the reaction container 4, a lens 52*c* for receiving light emitted from the reaction container 4 and guiding condensed light to the photodetector 48*c*, and a filter 54*c* for selecting light having a predetermined emission wavelength from the condensed light.

In the case of using such a detection unit 38*c*, chemiluminescence or bioluminescence emitted from a reaction product contained in the reaction container 4 is condensed by the lens 52*c*, and light having a predetermined emission wavelength is selected by the filter 54*c*, and the selected light is detected by the photodetector 48*c*.

FIGS. 10 to 14 show other examples different in the structure of the reaction plate. The reaction plate in the example described above is designed to allow a reaction product to be detected in the reaction container 4, but the reaction plates in the examples shown in FIGS. 10 to 14 further has an analysis section for analyzing a reaction product.

Figure 10A:
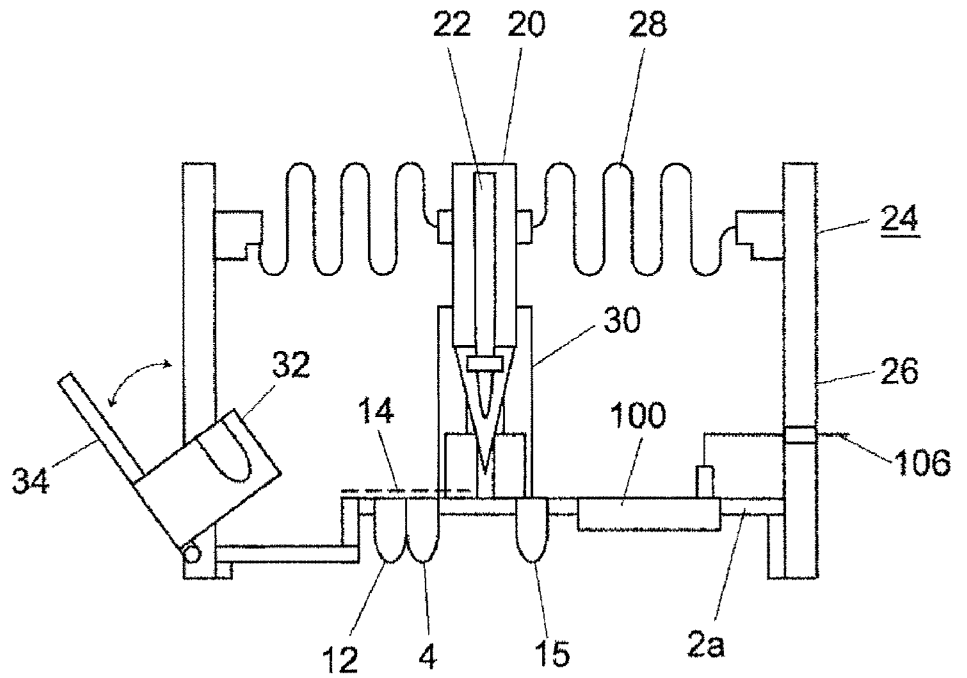
FIG. 10A is a vertical sectional view of another example of the reaction kit.
Figure 10B:
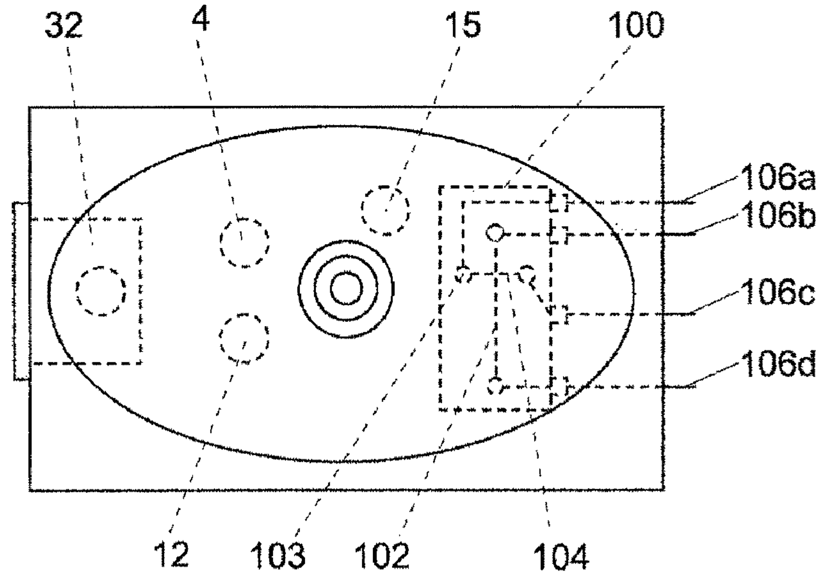
FIG. 10B is a plan view showing a reaction plate and a dispensation tip of the reaction kit shown in FIG. 10A.

A reaction plate 2*a* in the example shown in FIG. 10 has an electrophoresis section as the analysis section. In this case, an electrophoresis chip 100 is used as one example of the electrophoresis section. The electrophoresis chip 100 has a reaction product injection section 103, an electrophoretic separation channel 102, and electrodes 106*a* to 106*d* for applying an electrophoresis voltage. The electrophoresis chip 100 further has, in addition to the electrophoretic separation channel 102, a sample introduction channel 104 arranged so as to cross the channel 102 to introduce a sample into the channel 102, but the sample introduction channel 104 may have such a structure that a sample can be directly introduced thereinto from one end of the channel 102. The electrophoresis chip 100 is subjected to fluorescence detection from the back surface side thereof, and is therefore made of a low self-fluorescence and an optically-transparent resin such as polycarbonate, glass, or quartz.

The reaction plate 2*a* further has a separation buffer container 15 provided in the top surface thereof to receive a separation buffer to be injected into the channels 102 and 104. The separation buffer container 15 is sealed with a film through which the tip of the dispensation tip 20 can pass.

The electrodes 106*a* to 106*d* for applying an electrophoresis voltage are connected to both ends of the channel 102 and 104, respectively. These electrodes 106*a* to 106*d* are extended to the outside of the cover 24 so as to be connected to a power supply provided outside the reaction kit.

Each of the channels 102 and 104 has a reservoir at its end, and a separation buffer contained in the separation buffer container 15 is injected into the reservoirs.

In a case where the reaction kit is used for gene analysis, the reagent container 12 is allowed to previously contain a PCR reaction reagent. In this case, the reaction container 4 serves as a PCR reaction container.

In a case where a gene sample is measured using the example, a sample is introduced into the reaction kit from the sample container 32, and then the reaction kit is attached to the reaction kit treatment equipment. In the reaction kit treatment equipment, the sample contained in the sample container 32 is dispensed into the reaction container 4 by the dispensation tip 20, and then a PCR reaction reagent contained in the reagent container 12 is also dispensed into the reaction container 4 by the dispensation tip 20. Further, mineral oil (not shown) is layered over a mixture of the sample and the reagent contained in the reaction container 4, and then PCR reaction is carried out by controlling the temperature of the reaction mixture contained in the reaction container 4 according to a predetermined temperature cycle.

A separation buffer is supplied by the dispensation tip 20 from the separation buffer container 15 to the channels 102 and 104 through the reservoirs in the electrophoresis chip 100.

After the completion of the PCR reaction, an obtained reaction mixture is supplied as a sample by the dispensation tip 20 from the reaction container 4 to the injection section 103 of the electrophoresis chip 100 having the separation buffer previously supplied. Then, a voltage is applied from a power supply 101 (see FIG. 11) provided in the reaction kit treatment equipment to the channels 102 and 104 through the electrodes 106*a* to 106*d* to introduce the sample into the electrophoretic separation channel 102, and then the sample is electrophoresed in the channel 102 to be separated into its components.

In order to detect sample components separated by electrophoresis, the reaction kit treatment equipment has a detection unit 38*d*.

It is to be noted that in this case, the reaction container 4 is used as a PCR reaction container, but a PCR reaction container may be provided separately from the reaction container 4.

Figure 11:
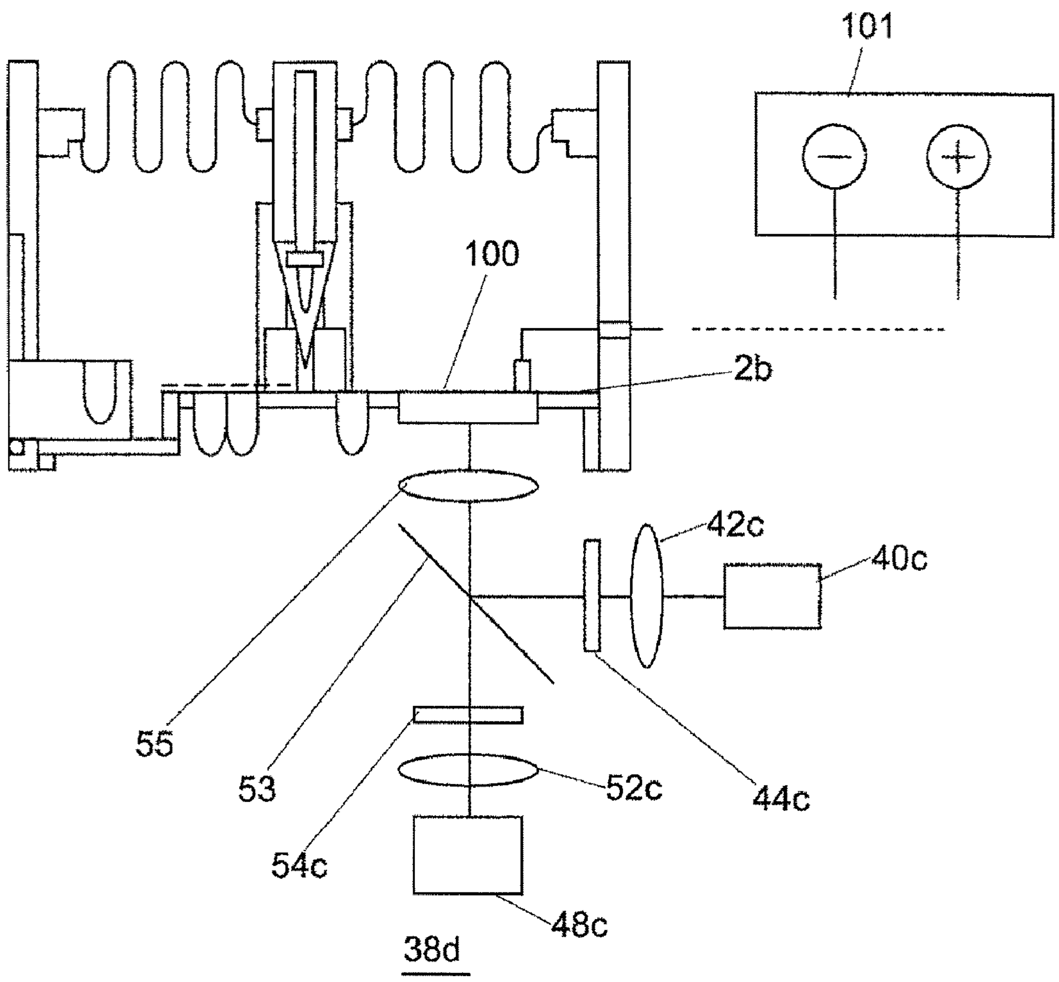
FIG. 11 is a vertical sectional view showing the reaction kit shown in FIG. 10A and an example of a detection unit used for the detection of a reaction product in the reaction kit according to the present invention.

The detection unit 38*d* is shown in FIG. 11. The detection unit 38*d* includes an excitation optical system and a fluorescence-receiving optical system to carry out fluorescence detection of sample components passing through a predetermined position in the electrophoretic separation channel 102. Since the detection unit 38*d* detects the fluorescence of sample components passing through a fixed position, it is not necessary to move the detection unit 38*d*.

The excitation optical system has a light source 40*c*, a lens 42*c* for condensing light emitted from the light source 40*c* to obtain parallel light, and a filter 44*c* provided on the optical path of parallel light beams obtained by the lens 42*c* to select light having a predetermined excitation wavelength from light emitted from the light source 40*c*.

The detection unit 38*d* further includes a dichroic mirror 53 and an objective lens 55 to irradiate a predetermined position in the electrophoretic separation channel 102 with excitation light obtained by the excitation optical system from the back surface side of the electrophoresis chip 100 and to receive fluorescence emitted from the position and convert it into parallel light. It is to be noted that the dichroic mirror 53 is designed so as to reflect light having an excitation wavelength to be used for the example and transmit light having a fluorescence wavelength.

The fluorescence-receiving optical system of the detection unit 38*d* is arranged at a position where it can receive fluorescence converted into parallel light by the objective lens 55 and passed through the dichroic mirror 53. The fluorescence-receiving optical system has a filter 54*c* for selecting light having a predetermined fluorescence wavelength from fluorescence passed through the dichroic mirror 53 and a lens 52*c* for condensing the fluorescence having a wavelength selected by the filter 54*c* to introduce condensed light into a detector 48*c*. As described above, the reason for once converting light into parallel light by the lenses 42*c* and 55 is to improve the precision of wavelength selection by the filters 44*c* and 54*c*.

In the case of using such a detection unit 38*d*, light having an excitation wavelength for exciting a reaction product is selected by the filter 44*c* from light emitted from the light source 40*c* to irradiate the reaction product passing through a predetermined position in the electrophoretic separation channel 102 with the light, and fluorescence emitted from the reaction product is received by the light-receiving optical system, and light having a predetermined fluorescence wavelength is selected by the filter 54*c* and detected by the photodetector 48*c*.

Figure 12A:
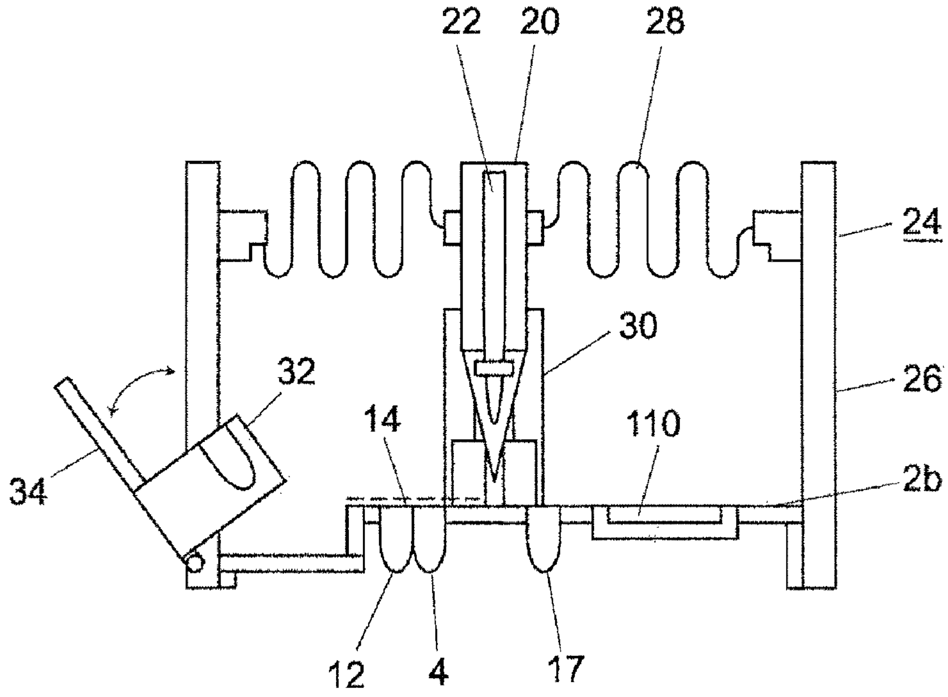
FIG. 12A is a vertical sectional view of another example of the reaction kit.
Figure 12B:
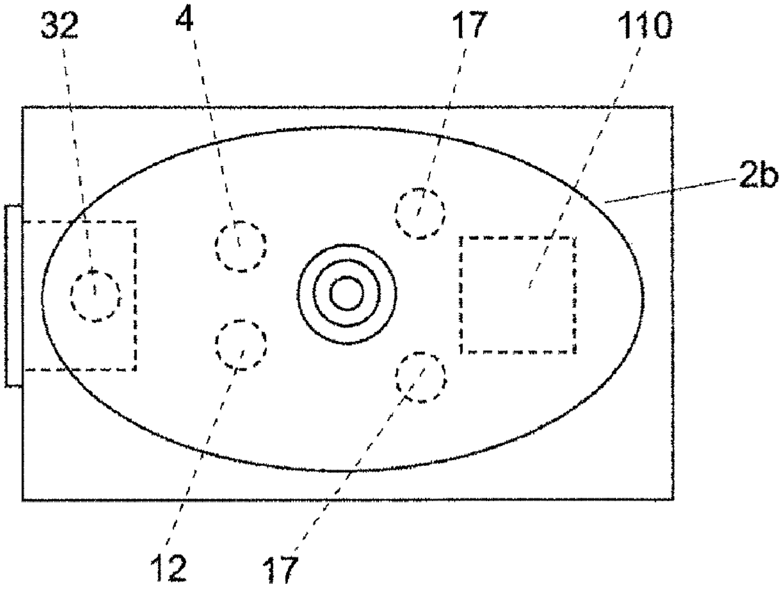
FIG. 12B is a plan view showing a reaction plate and a dispensation tip of the reaction kit shown in FIG. 12A.

A reaction plate 2*b* of the reaction kit of the example shown in FIGS. 12A and 12B has a DNA chip 110 as the analysis section. When a reaction product contains a gene, probes, which react with the gene, are immobilized to the DNA chip 110. The DNA chip 110 is subjected to fluorescence detection from the back surface side thereof, and is therefore made of a low self-fluorescence and an optically-transparent resin such as polycarbonate or glass.

The reaction plate 2*b* further has cleaning solution containers 17 formed in the top surface thereof. The cleaning solution containers 17 contain a cleaning solution for separating and removing the reaction product not having been bound to the probes from the reaction product having been bound to the probes in the DNA chip 110. Further, the cleaning solution containers 17 are sealed with a film through which the tip of the dispensation tip 20 can pass.

In a case where the example is used for gene analysis, the reagent container 12 is allowed to previously contain a PCR reaction reagent. In this case, the reaction container 4 serves as a PCR reaction container.

In a case where a gene sample is measured using the reaction kit of the example, the sample is introduced into the reaction kit from the sample container 32, and then the reaction kit is attached to the reaction kit treatment equipment. In the reaction kit treatment equipment, the sample contained in the sample container 32 is dispensed into the reaction container 4 by the dispensation tip 20, and then a PCR reaction reagent contained in the reagent container 12 is also dispensed into the reaction container 4 by the dispensation tip 20. Further, mineral oil (not shown) is layered onto a mixture of the sample and the reagent contained in the reaction container 4, and then PCR reaction is carried out by controlling the temperature of the mixture contained in the reaction container 4 according to a predetermined temperature cycle.

After the completion of the PCR reaction, an obtained reaction mixture is supplied as a sample from the reaction container 4 to the DNA chip 110 by the dispensation tip 20. After the completion of incubation, a cleaning solution is supplied from the cleaning solution container 17 to the DNA chip 110 by the dispensation tip 20, and then a reaction product not having been bound to the probes is removed by sucking the cleaning solution into the dispensation tip 20.

The reaction product having been bound to the probes can be detected by fluorescence by previously labeling the reaction product with a fluorescent material. The detection of the presence of fluorescence in the DNA chip 110 indicates that a gene corresponding to the probe immobilized at a position where fluorescence has been detected is contained in the sample.

In order to detect the reaction product having been bound to the probes in the DNA chip 110, the reaction kit treatment equipment includes a detection unit 38*e*.

Figure 13:
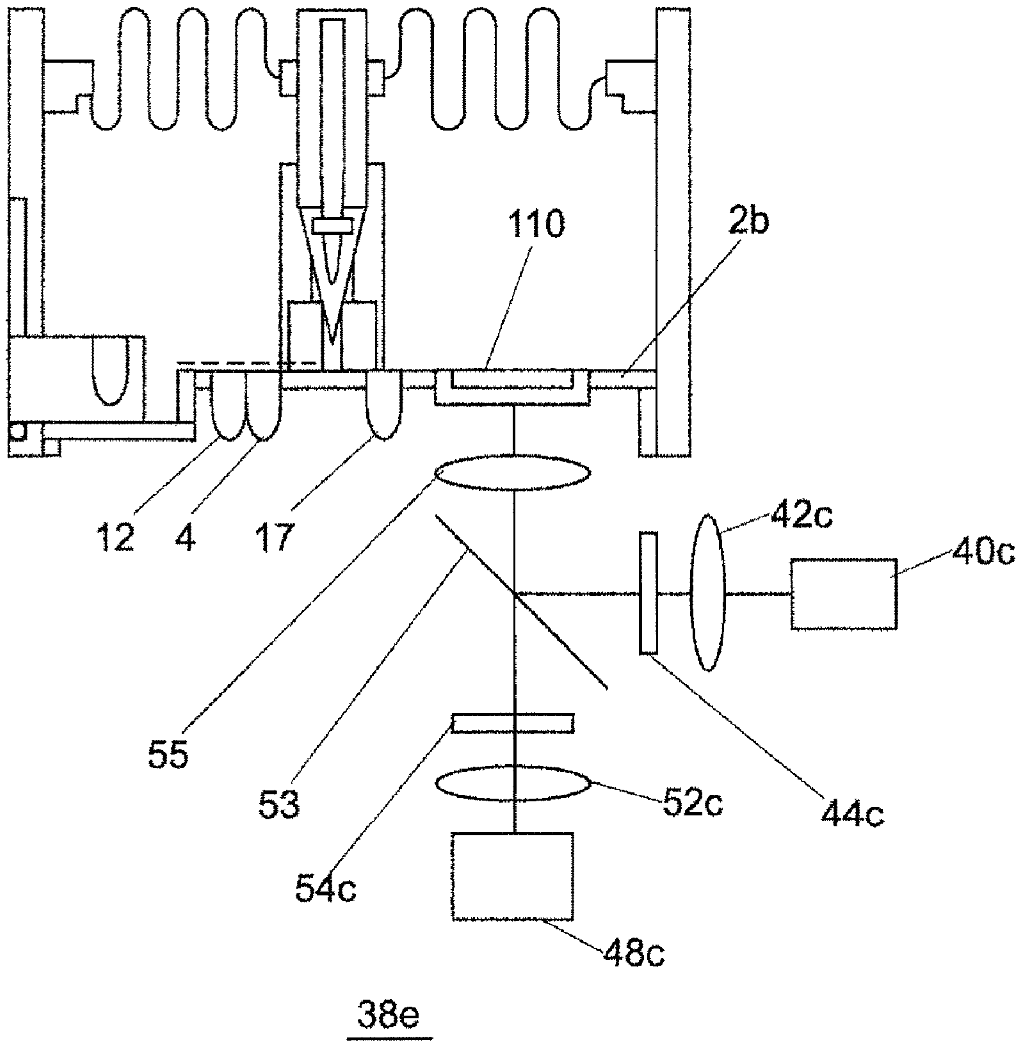
FIG. 13 is a vertical sectional view showing the reaction kit shown in FIG. 12A and an example of the detection unit used for the detection of a reaction product in the reaction kit according to the present invention.
Figure 20:
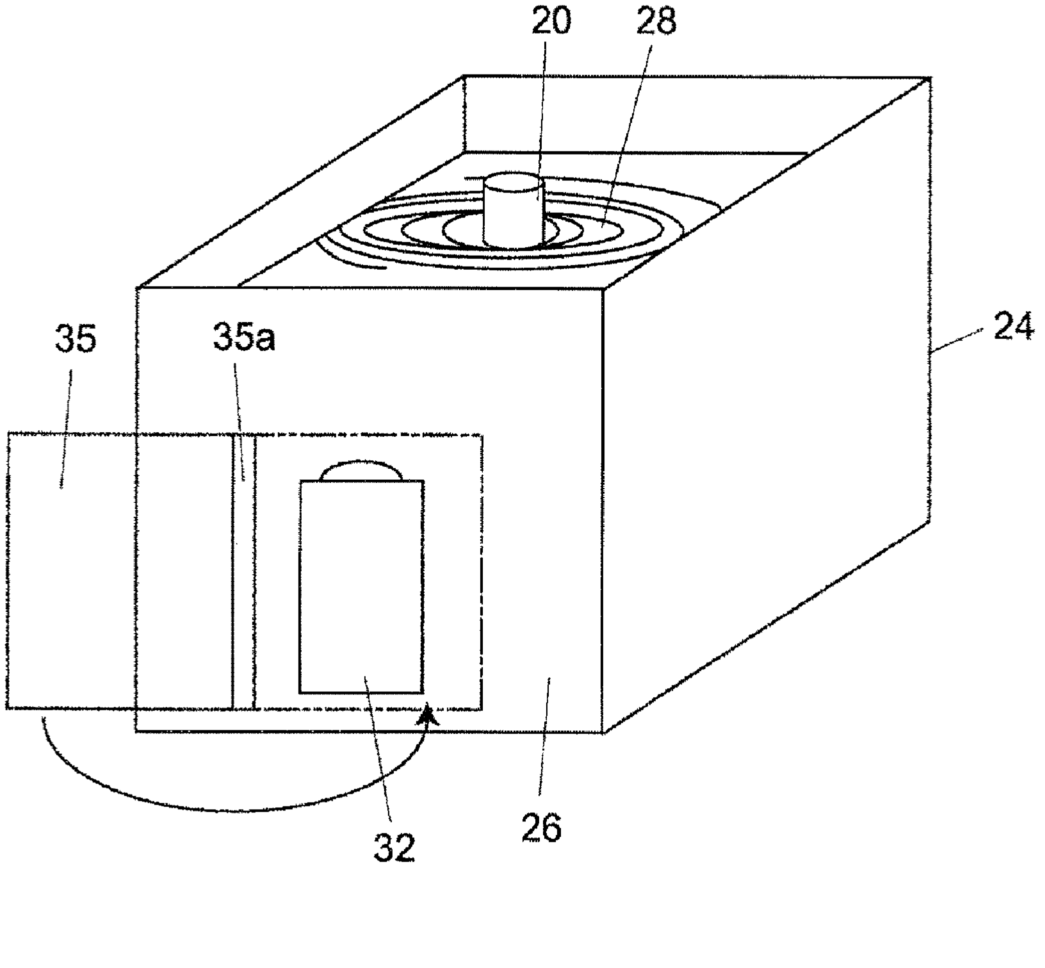
FIG. 20 is a perspective view showing the appearance of another example of the reaction kit.

The detection unit 38*e* is shown in FIG. 13. The structure of an optical system of the detection unit 38*e* is the same as that of the detection unit 38*d* shown in FIG. 11, and therefore the description thereof is omitted. The detection unit 38*e* is different from the detection unit 38*d* shown in FIG. 11 in that it is movably supported so that fluorescence detection can be carried out for all the probes arranged in the DNA chip 110. Such detection can be achieved, as shown in FIG. 20, by allowing a table 82 to move in the X direction and by allowing the detection unit 38*e* to move in the Y direction.

Figure 14:
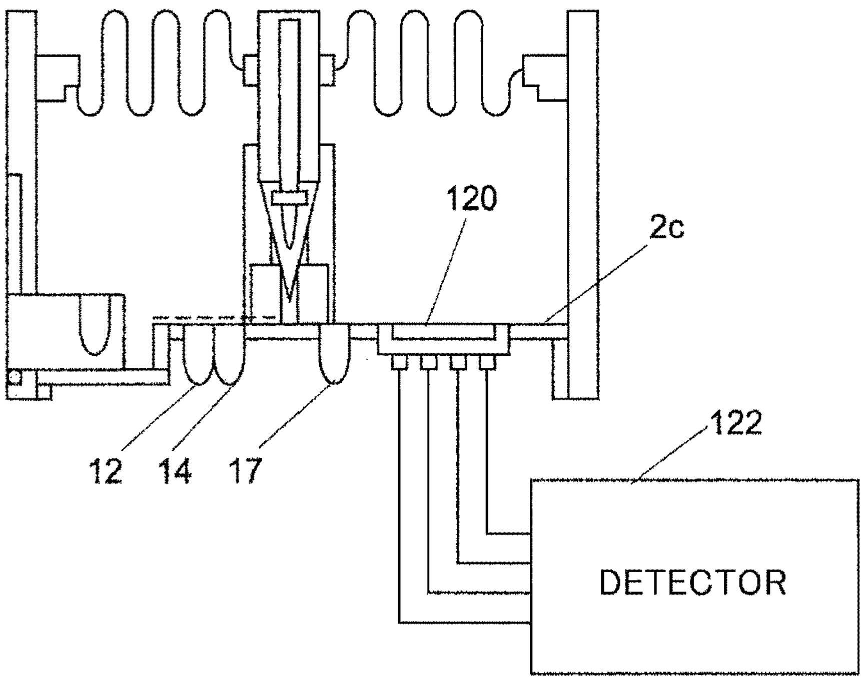
FIG. 14 is a vertical sectional view showing another example of the reaction kit and another example of the detection unit used for the detection of a reaction product in the reaction kit according to the present invention.

A reaction plate 2*c* of the example shown in FIG. 14 has a DNA chip 120 as the analysis section. The DNA chip 120 is different from the DNA chip 110 of the reaction kit shown in FIG. 12 in that it is designed to allow a reaction product to be detected not by fluorescence detection but by electric detection. The DNA chip 120 utilizes a phenomenon in which the current value of each probe varies depending on whether a sample gene has been bound to the probe or not. Since the DNA chip 120 is not subjected to optical detection, the material of the DNA chip 120 does not need to be optically transparent but needs to be electrically insulating.

When a reaction product contains a gene, probes, which react with the gene, are immobilized to the DNA chip 120. Each of the probes is connected to an electrode provided on the back surface of the reaction plate so that the current value thereof can be measured. In the case of using the reaction kit, it is not necessary to previously label a sample with a fluorescent material.

The electrodes provided on the back surface of the reaction plate and connected to the probes are connected also to a detector 122 provided in the reaction kit treatment equipment to measure the current value of each of the probes to detect the reaction product in the DNA chip 120.

The reaction plate 2*c* also has a cleaning solution container 17 formed in the top surface thereof. The cleaning solution container 17 contains a cleaning solution for separating the reaction product not having been bound to the probes immobilized to the DNA chip 120 from the reaction product having been bound to the probes and removing the former from the DNA chip 120. Further, the cleaning solution container 17 is sealed with a film through which the tip of the dispensation tip 20 can pass. The reagent container 12 previously contains a PCR reaction reagent. The reaction container 4 serves as a PCR reaction container.

In a case where a gene sample is measured by the example, the sample is introduced into the reaction kit from the sample container 32, and then the reaction kit is attached to the reaction kit treatment equipment. In the reaction kit treatment equipment, the sample contained in the sample container 32 is dispensed into the reaction container 4 by the dispensation tip 20, and then a PCR reaction reagent contained in the reagent container 12 is also dispensed into the reaction container 4 by the dispensation tip 20. Further, mineral oil (not shown) is layered onto a mixture of the sample and the reagent contained in the reaction container 4, and then PCR reaction is performed by controlling the temperature of the mixture contained in the reaction container 4 according to a predetermined temperature cycle.

After the completion of the PCR reaction, an obtained reaction mixture is supplied as a sample from the reaction container 4 to the DNA chip 120 by the dispensation tip 20. Then, a cleaning solution is supplied from the cleaning solution container 17 to the DNA chip 120 by the dispensation tip 20, and then a reaction product not having been bound to the probes is removed by sucking the cleaning solution into the dispensation tip 20.

In order to detect the reaction product having been bound to the probes in the DNA chip 120, the reaction kit treatment equipment includes a detector 122. After the reaction product not having been bound to the probes is removed, the current value of each probe is measured by the detector 122.

It is to be noted that a gene sample can be measured even when the DNA chip 110 or 120 of the reaction kit shown in FIG. 12 or 14 is replaced with a hybridization region.

Figure 15:
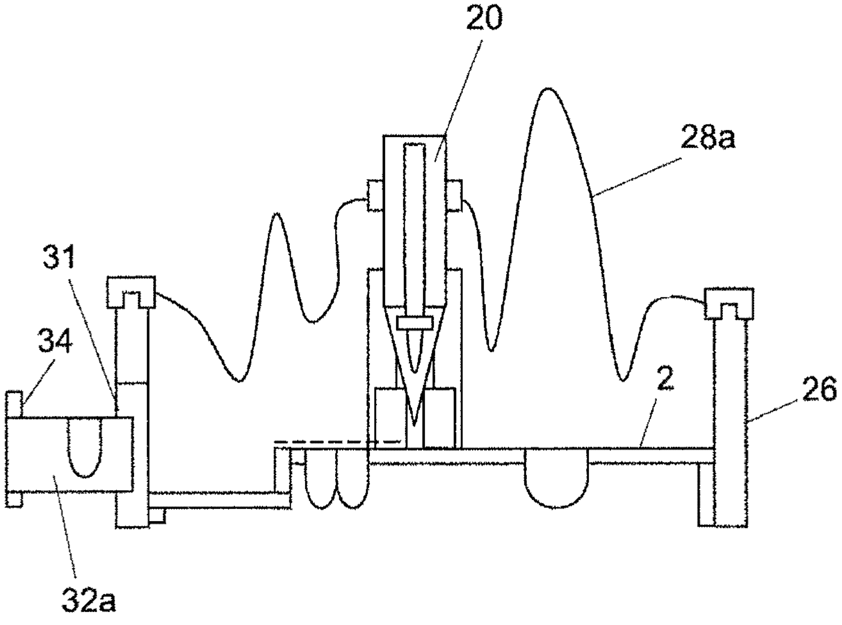
FIG. 15 is a vertical sectional view of another example of the reaction kit.

FIG. 15 shows another example different in the structure of the cover. More specifically, the reaction kit shown in FIG. 1 has a bellows film 28 as part of the cover movably supporting the dispensation tip 20 and covering a space above the reaction plate 2, but the example shown in FIG. 15 has a flexibly deformable film 28a as part of the cover. As in the case of the bellows film 28, the film 28*a* is preferably made of nylon, polyvinyl chloride, or a rubber material such as silicone rubber.

Further, the example shown in FIG. 15 is different from the example shown in FIG. 1 also in the structure of the sample container. More specifically, in the case of the reaction kit shown in FIG. 1, one side of the sample container is rotatably supported by the cover main body 26, but a sample container 32*a* of the reaction kit shown in FIG. 15 is slidably attached to the cover main body 26. Also, in the case of such a sample container 32*a*, a sample can be dispensed into the sample container 32*a* by pulling the sample container 32*a* toward the outside of the cover main body 26. The sample container 32*a* of the reaction kit shown in FIG. 15 is the same as the sample container 32 of the example shown in FIG. 1 in that the opening 31 of the cover main body 26 can be closed by sliding the sample container 32*a* toward the inside of the cover main body 26 and can be sealed by bringing the plate 34 into intimate contact with the cover main body 26 using a pressure-sensitive adhesive previously applied onto the inner surface of the plate 34 or by using a sealant.

The detection unit 38*a*, 38*b*, or 38*c* is arranged in the reaction kit treatment equipment so as to be located under the reaction plate 2 of the reaction kit attached to the treatment equipment.

Figure 16A:
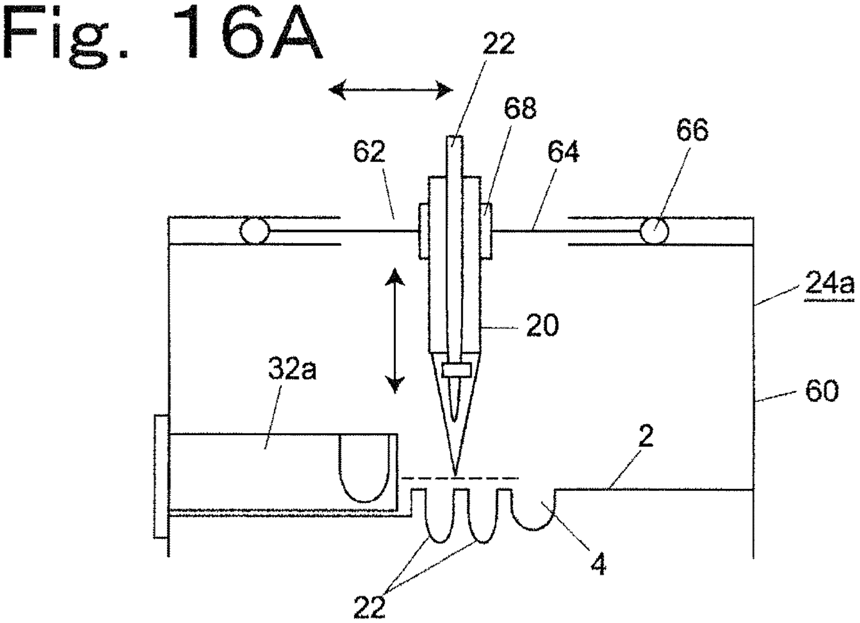
FIG. 16A is a vertical sectional view of another example of the reaction kit.
Figure 16B:
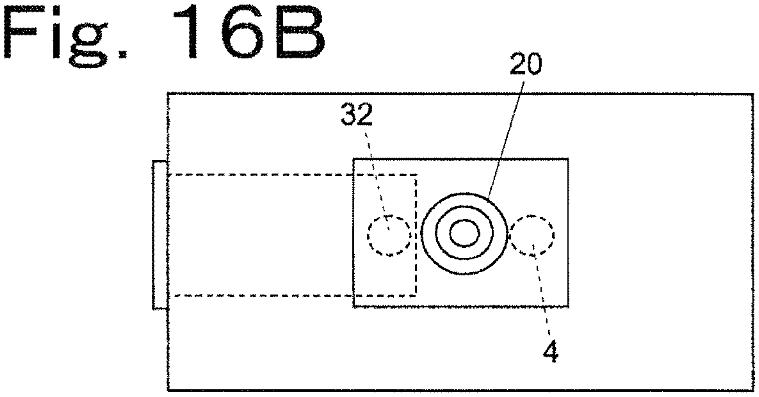
FIG. 16B is a plan view showing a reaction plate and a dispensation tip of the reaction kit shown in FIG. 16A.
Figure 16C:
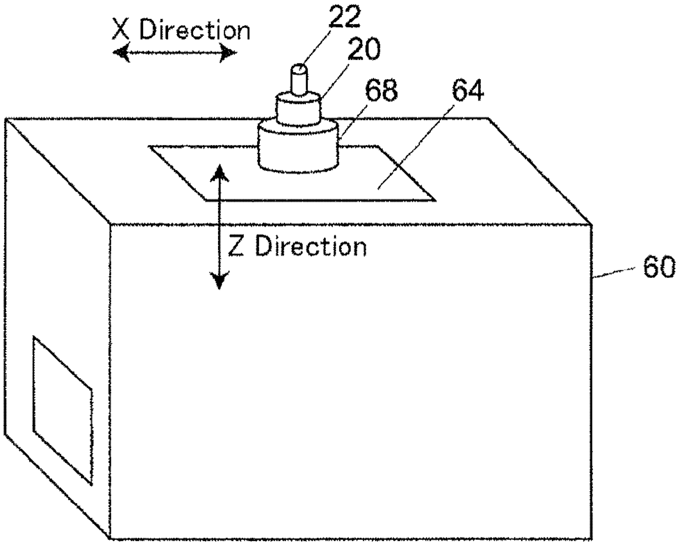
FIG. 16C is a perspective view showing the appearance of the reaction kit shown in FIG. 16A.

FIGS. 16A-16C show another example of a reaction kit, in which FIG. 16A is a vertical sectional view, FIG. 16B is a horizontal sectional view of the reaction kit shown in FIG. 16A, and FIG. 16C is a perspective view showing the appearance of the reaction kit shown in FIG. 16A.

The example has a cover movably supporting the dispensation tip 20, and the cover is made of a material having stiffness. A cover main body 60 of a cover 24*a* has an opening 62 located above the reaction plate 2. In the opening 62, a cover plate 64 for movably supporting the dispensation tip 20 is provided so that the dispensation tip 20 can be moved within a range defined by the opening 62. A part of the cover main body 60 around the opening 62 has a double structure having an interior gap, and a sealant 66 is provided around the periphery of the cover plate 64. The sealant 66 is moved in the X direction in the interior gap of the double structure provided around the opening 62 of the cover main body 60, which allows the cover plate 64 to move in the X direction in a horizontal plane. Further, the dispensation tip 20 is supported by the cover plate 64 by means of another sealant 68, which is interposed between the dispensation tip 20 and the cover plate 64, so as to be able to slide in the vertical direction (Z direction).

In the example, the cover plate 64 is moved in a horizontal plane while the reaction kit is kept hermetically sealed by a sealing structure constituted from the cover plate 64, the sealant 66, and the interior gap of the double structure provided in the upper part of the cover main body 60, and the dispensation tip 20 is moved in the vertical direction while the reaction kit is kept hermetically sealed by the sealant 68. This makes it possible to freely move the dispensation tip 20 in a space above the reaction plate 2 in two directions, i.e., in the vertical direction and a direction in a horizontal plane.

Figure 17A:
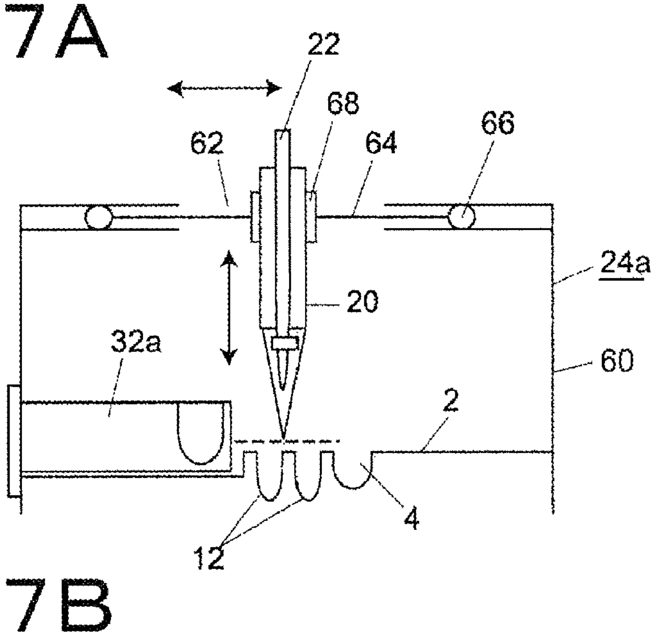
FIG. 17A is a vertical sectional view of another example of the reaction kit.
Figure 17B:
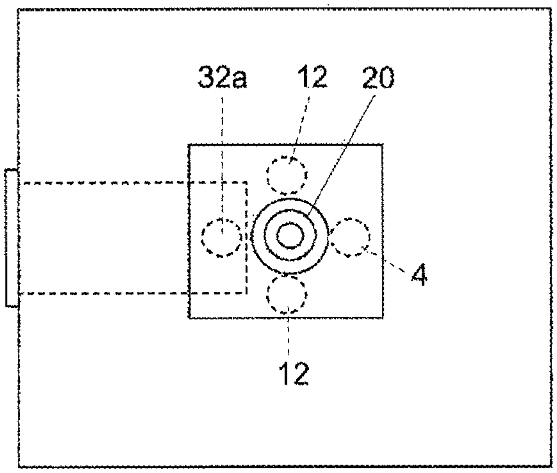
FIG. 17B is a plan view showing a reaction plate and a dispensation tip of the reaction kit shown in FIG. 17A.
Figure 17C:
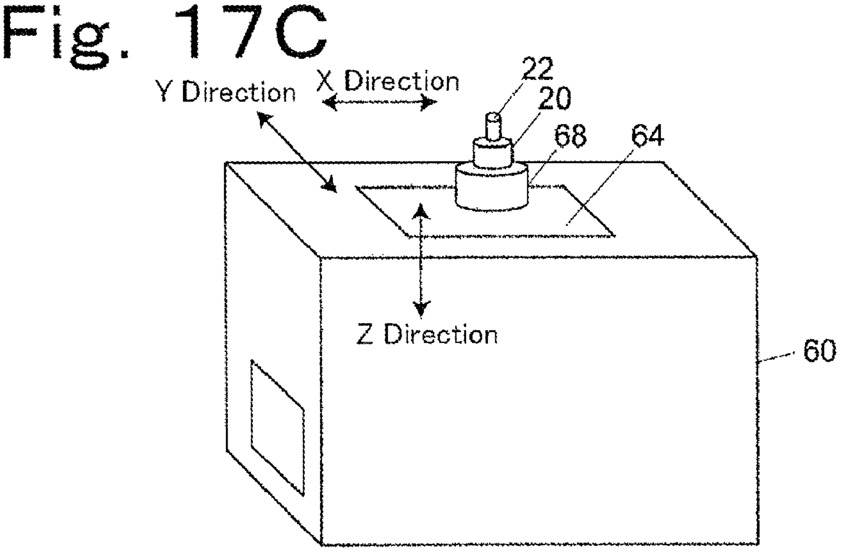
FIG. 17C is a perspective view showing the appearance of the reaction kit shown in FIG. 17A.

FIGS. 17A-17C show another example of a reaction kit. The reaction kit shown in FIG. 17 is the same as the reaction kit shown in FIG. 16 except that the cover plate 64 can be moved in two directions, i.e., X and Y directions, and that the number of the reagent containers 12 provided in the reaction plate 2 is increased.

Figure 18A:
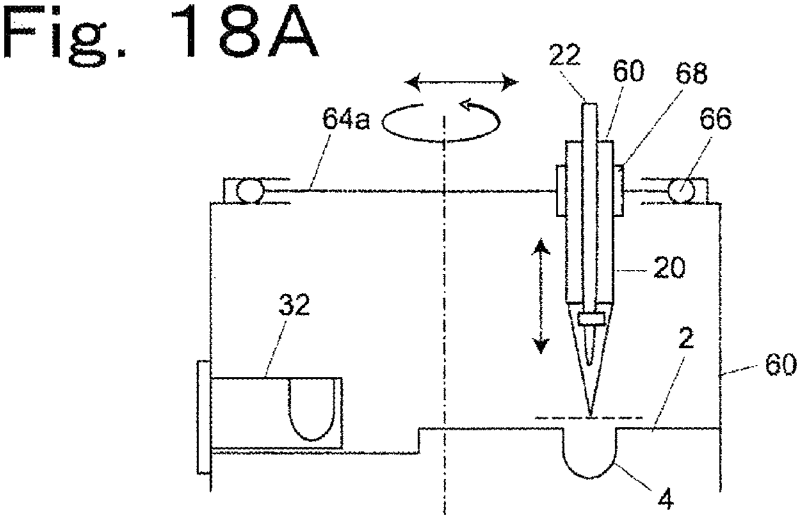
FIG. 18A is a vertical sectional view of another example of the reaction kit.
Figure 18B:
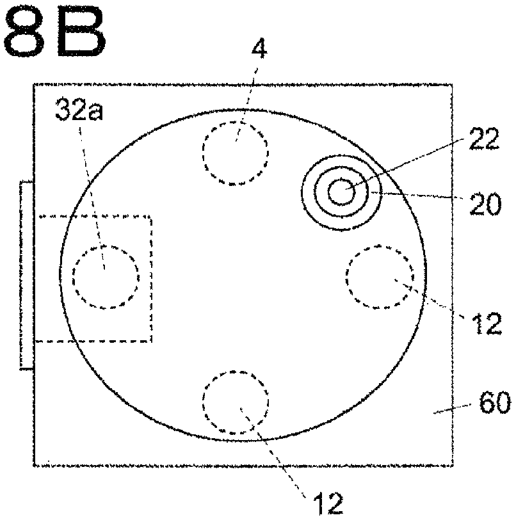
FIG. 18B is a plan view showing a reaction plate and a dispensation tip of the reaction kit shown in FIG. 18A.
Figure 18C:
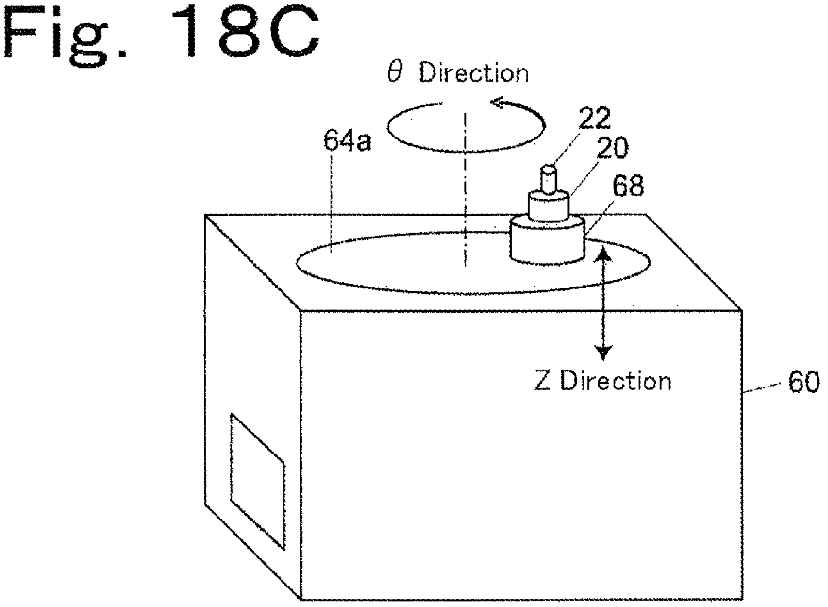
FIG. 18C is a perspective view showing the appearance of the reaction kit shown in FIG. 18A.

FIGS. 18A-18C show another example. The example shown in FIGS. 18A-18C is different from the example shown in FIGS. 16A-16C in that a cover plate 64*a* as an upper member of the cover is supported so as to be able to rotate in the in-plane direction to move the dispensation tip 20 in the in-plane direction. The cover plate 64*a* has a disc shape, and the sealant 66 is attached to the periphery of the cover plate 64*a*. The sealant 66 is held in the interior gap of the double structure provided in the upper part of the cover main body 60, and rotatably supports the cover plate 64*a* while keeping the reaction kit hermetically sealed. The dispensation tip 20 is supported by the cover plate 64*a* by means of the sealant 68 so as to be able to move in the vertical direction. The dispensation tip 20 supported by the cover plate 64*a* is located off the center of rotation of the cover plate 64*a*.

By rotating the cover plate 64*a*, it is possible to move the dispensation tip 20 on the circumference of a circle whose center is the rotational center of the cover plate 64*a*. Therefore, the reaction container 4 and the reagent containers 12 provided in the reaction plate 2 and the sample container 32 are arranged so as to be located on the movement locus of the dispensation tip 20.

Figure 19A:
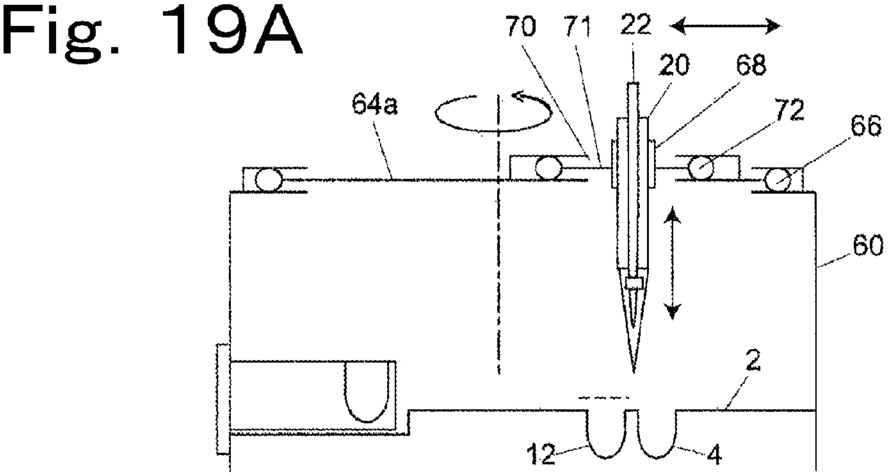
FIG. 19A is a vertical sectional view of another example of the reaction kit.
Figure 19B:
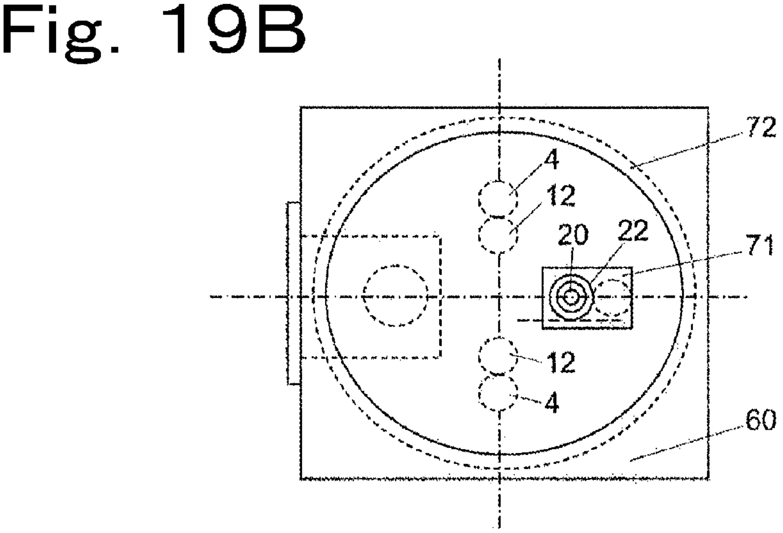
FIG. 19B is a plan view showing a reaction plate and a dispensation tip of the reaction kit shown in FIG. 19A.
Figure 19C:
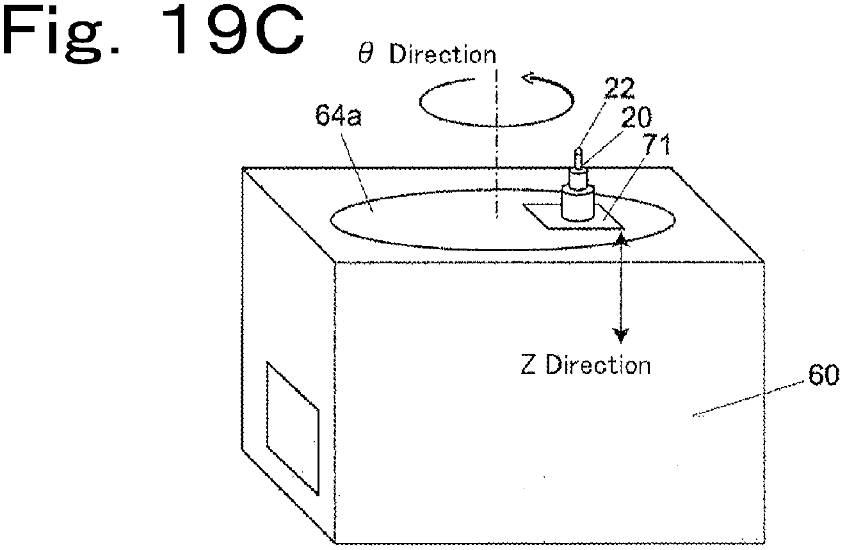
FIG. 19C is a perspective view showing the appearance of the reaction kit shown in FIG. 19A.

FIGS. 19A-19C show another example. The example shown in FIGS. 19A-19C is different from the example shown in FIGS. 18A-18C in that the cover plate 64*a* also has an opening 70, a double structure having an interior gap is provided around the opening 70, and another cover plate 71 is movably supported by the double structure by means of a sealant 72 held in the interior gap of the double structure. The dispensation tip 20 is supported by the cover plate 71 by means of another sealant 68 so as to be able to move in the vertical direction.

The dispensation tip 20 can be moved also in the in-plane direction by the sealant 72. Therefore, the dispensation tip 20 can be moved within a range defined by both the circumference of a circle obtained by rotating the cover plate 64*a* and a horizontal plane obtained by moving the smaller cover plate 71 movable by the sealant 72, that is, within a doughnut-shaped range whose center is the rotational center of the cover plate 64*a*. In the case of the reaction kit shown in FIG. 19, the moving range of the dispensation tip 20 becomes larger, and therefore it is possible to increase the numbers of the reaction containers 4 and the reagent containers 12 arranged in the moving range of the dispensation tip 20. In addition, it is also possible to increase the degree of freedom of arrangement of these containers and the sample container 32.

FIG. 20 is a perspective view showing the appearance of another embodiment of the reaction container according to the present invention. The internal structure of the reaction container shown in FIG. 20 is the same as that shown in FIG. 1A. A cover main body 26 has an opening 31 for supplying a sample onto a reaction plate 2 from the outside of a cover 24. A sample container 32 is attached to the opening 31, and therefore the opening 31 can be closed by the sample container 32. In order to hermetically seal the opening 31 closed by the sample container 32 after a sample is introduced into a space covered with the cover 24, a sealing member 35 to be adhered to the cover main body 26 is provided outside the cover main body 26 to cover the outside of the sample container 32. It is noted that a part 35*a* of the sealing member 35 is previously adhered to the cover main body 26. The sealing member 35 has a surface coated with an adhesive, and the adhesive-coated surface is being covered with a release sheet until the sealing member 35 is used.

As a concrete example of the sealing member 35, one obtained by applying an adhesive to a base material can be mentioned. Examples of the base material used include polyethylene film, polypropylene film, polystyrene film, synthetic paper, polyimide film, and film for variable information printing. Examples of the adhesive applied onto the base material include PVA-based emulsions, SBR-based emulsions, acrylic emulsions, synthetic rubber-based emulsions, pressure-sensitive adhesives, and heat-sensitive adhesives.

The sample container 32 has a recess having an opening in the top surface thereof to receive a sample. After a sample is injected into the recess, the sample container 32 is placed inside the cover 24, and therefore the opening 31 is closed by a plate 34 holding the sample container 32. Then, the release sheet attached to the adhesive-coated surface of the sealing member 35 is removed, and the sealing member 35 is adhered to the cover main body 26 so as to cover the plate 34. In this way, the opening 31 is hermetically sealed with the sealing member 35.

Further, the bellows film 28 of the reaction kit shown in FIG. 20 has a surface having been treated by polyparaxylylene resin coating or fluorocarbon resin coating to reduce a coefficient of friction.

The polyparaxylylene resin coating refers to surface coating using a polyparaxylylene resin. This coating material has the following characteristics: (1) being a crystalline polymer; (2) having high water repellency and excellent gas barrier properties; (3) having high chemical resistance; (4) having excellent electric properties; (5) having excellent heat stability; (6) having excellent low-temperature properties; (7) having excellent vacuum stability; and (8) having high resistance to radiation.

In particular, polyparaxylylene resin coating exhibits excellent gas barrier properties. For example, the permeabilities of polyparaxylylene resin coating to gases of $N_2$, $CO_2$, and $H_2O$ are 1.0, 7.7, and 0.21, respectively, whereas the permeabilities of polypropylene resin coating to gases of $N_2$, $CO_2$, and $H_2O$ are 20, 540, and 0.25, respectively. That is, the permeabilities of polyparaxylylene resin coating to these gases are lower than those of polypropylene resin coating to these gases.

Such polyparaxylylene resin coating can be formed by a vapor deposition method described below.

A solid diparaxylylene dimer (DPX) is prepared as a raw material, and diradical paraxylylene is simultaneously adsorbed and polymerized on the surface of an adherend material by subliming the solid diparaxylylene dimer as a raw material or by generating a diradical paraxylylene monomer by thermal decomposition of the solid diparaxylylene dimer. In this way, a high-molecular-weight polyparaxylylene film is formed by polymerization.

This coating system based on the vapor deposition method described above is excellent in that molecular level fine coating impossible by conventional liquid or powder coating methods can be achieved, it is applicable irrespective of the shape or material of an adherend, and room-temperature coating is possible.

Figure 21A:
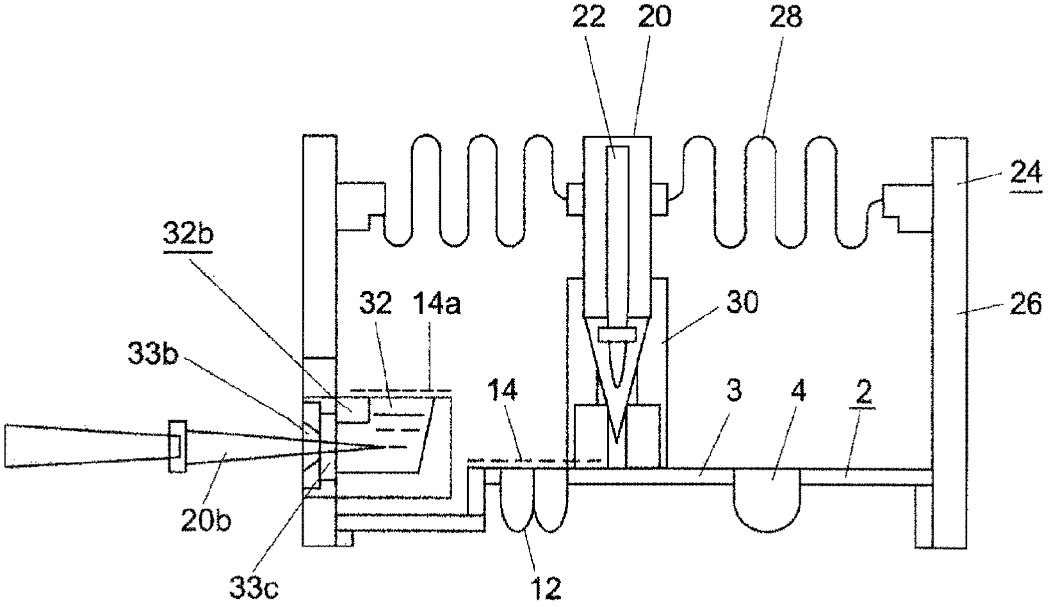
FIG. 21A is a vertical sectional view of another example of the reaction kit.
Figure 21B:
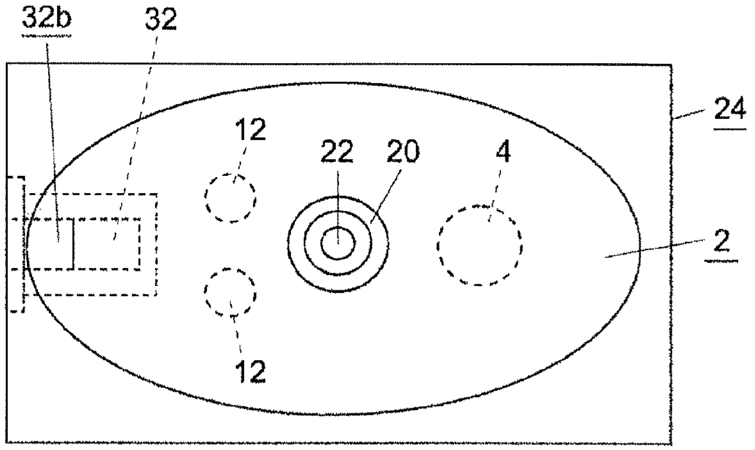
FIG. 21B is a plan view showing a reaction plate and a dispensation tip of the reaction kit shown in FIG. 21A.
Figure 22:
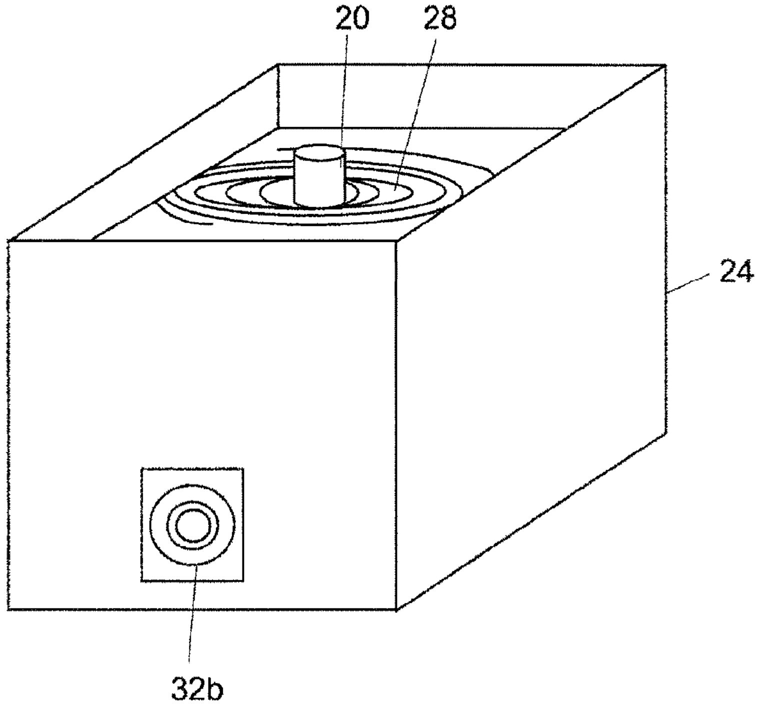
FIG. 22 is a perspective view showing the appearance of the reaction kit shown in FIG. 21A.

FIGS. 21A and 21B show another embodiment of the reaction kit according to the present invention, and FIG. 22 is a perspective view of the reaction kit shown in FIG. 21. The structure of the reaction kit shown in FIG. 21 is the same as that of the reaction kit shown in FIG. 1A except for a sample introduction unit. Hereinbelow, the sample introduction unit of the reaction kit shown in FIG. 21 will be described.

In a part of a cover main body 26, a sample introduction unit 32*b* for introducing a sample from the outside into the reaction kit through a sample introduction port 33*b* is provided. The sample introduction port 33*b* is sealed with an elastic member 33*c* through which a sharp-tipped dispensation tool 20*b* for injecting a sample, e.g., a dispensation tip attached to the tip of a pipetter, can pass to form a through hole closable by pulling out the dispensation tool 20*b* due to its elasticity. Therefore, the sample introduction port 33*b* is kept hermetically sealed not only when the dispensation tool 20*b* is being passed through the elastic member 33*c* but also after the dispensation tool 20 is pulled out of the elastic member 33*c*. The sample introduction port 33*b* is provided in a plate member as a hole tapered from the inside toward the outside of the reaction kit. The elastic member 33*c* is, for example, a rubber septum, and is fixed by being sandwiched between the plate member having the sample introduction port 33*b* and the sample introduction unit 32*b*.

In a case where the dispensation tool 20*b* is used with a dispensation tip being attached to the tip thereof, the dispensation tip is conceptually included in the dispensation tool. Therefore, in this case, the elastic member 33*c* of the sample introduction port 33*b* is designed to allow the dispensation tip to pass through it.

The sample introduction unit 32*b* constitutes a sample container 32. The side surface of the sample container 32 has the sample introduction port 33*b* and the upper part of the sample container 32 has an opening for use in dispensing a sample contained in the sample container 32 into a predetermined portion on the reaction plate. The opening of the sample container 32 is covered with a cover film 14*a*. In the sample container 32, a sample pretreatment solution or a reagent is previously contained.

By covering the opening of the sample container 32 with the cover film 14*a*, it is possible to prevent a sample pretreatment solution or a regent from spilling over the sample container 32 during transport or storage of the reaction kit.

As the cover film 14*a*, an aluminum film used also as the film 14 can be used.

Figure 23:
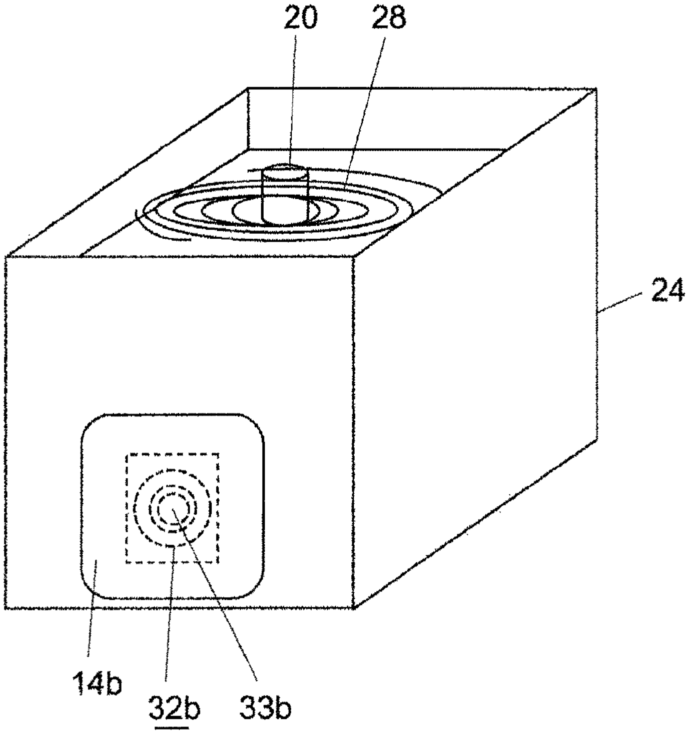
FIG. 23 is a perspective view showing the appearance of the reaction kit shown in FIG. 21A in a state after a sample is introduced into the reaction kit.

As shown in FIG. 23, the sample introduction port 33*b* can be hermetically sealed with a sealing film 14*b* after a sample is introduced into the reaction kit through the sample introduction port 33*b*. Thus, it is possible to prevent the release of the sample (e.g., blood) attached to the elastic member 33*c* into an outside environment and thus to prevent the pollution of an outside environment with the sample.

As a concrete example of the sealing film 14*b*, one obtained by applying an adhesive onto a base material can be mentioned. Examples of the base material used include polyethylene film, polypropylene film, polystyrene film, synthetic paper, polyimide film, and film for variable information printing. Examples of the adhesive applied onto the base material include PVA-based emulsions, SBR-based emulsions, acrylic emulsions, synthetic rubber-based emulsions, pressure-sensitive adhesives, and heat-sensitive adhesives.

The sealing film 14*b* may be previously adhered to the cover main body 26. In this case, the sealing film 14*b* is temporarily peeled off during sample injection, and is again adhered to the cover main body 26 after the completion of sample injection to hermetically seal the sample introduction port 33*b*. The sealing film 14*b* to be previously adhered to the cover main body 26 is preferably formed by applying, onto a base material, a pressure-sensitive adhesive allowing the sealing film 14*b* to be easily peeled off from the cover main body 26.

Alternatively, the sealing film 14*b* may be separately prepared without being adhered to the cover main body 26 before sample injection. In this case, the sealing film 14*b* is being attached to a release sheet easily removable from the sealing film 14*b* until being used, and after the completion of sample injection, the release sheet is removed from the sealing film 14*b* and then the sealing film 14*b* is adhered to the cover main body 26 to hermetically seal the sample introduction port 33*b*.

Figure 24:
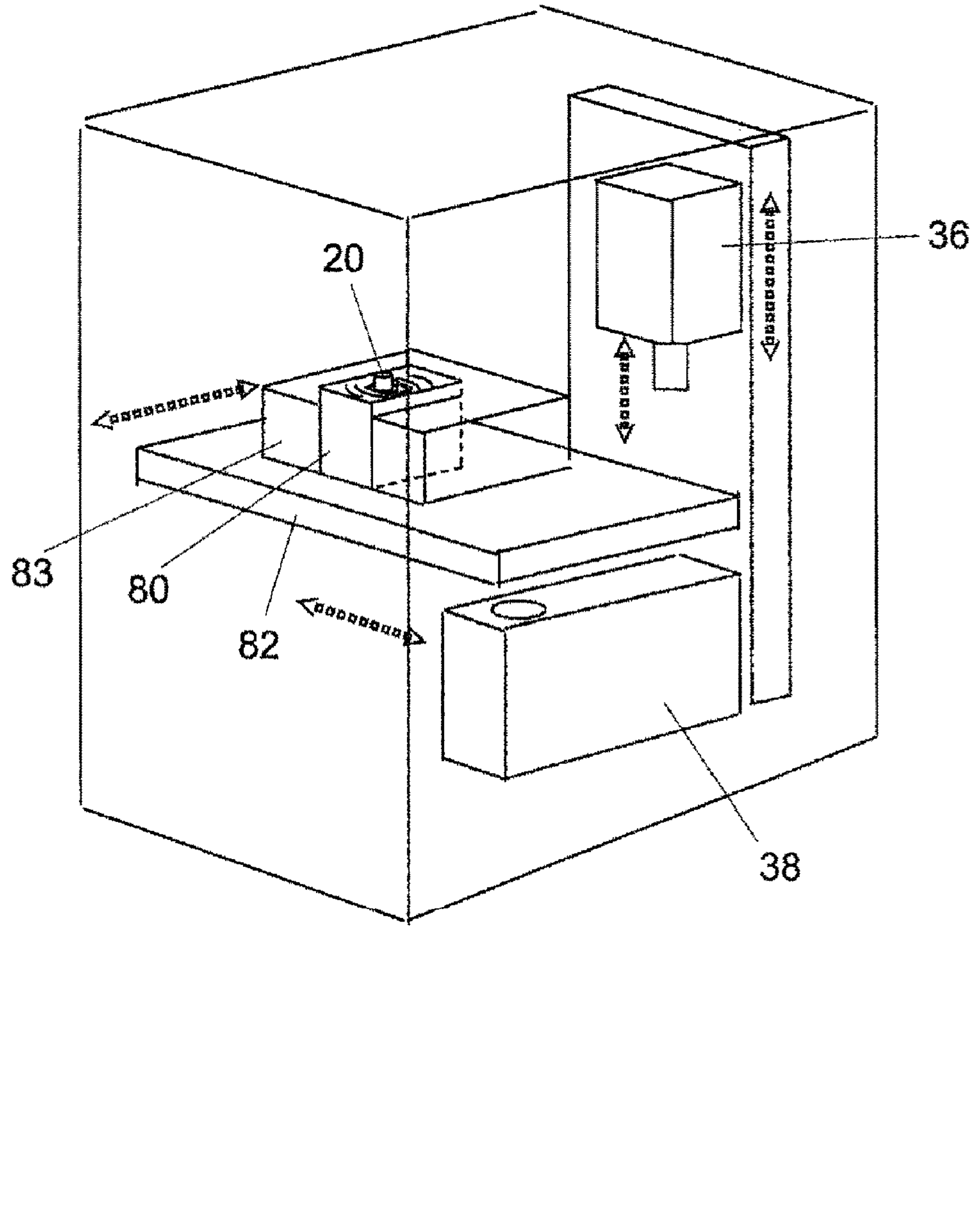
FIG. 24 is a perspective view schematically showing the interior structure of an example of the reaction kit treatment equipment.

FIG. 24 is a perspective view schematically showing the interior structure of one example of reaction kit treatment equipment for processing the reaction kits according to the present invention.

The reference numeral 80 denotes the reaction kit described above. The reaction kit 80 is attached onto a table 82 provided as a reaction kit attachment section. The table 82 has an opening in its surface facing the lower surface of the reaction kit 80. Under the table 82, a detection unit 38 is arranged to optically detect a reaction product contained in the reaction container 4 of the reaction kit 82. On the table 82, a temperature control unit 83 is arranged to control the temperature of the reaction kit 82. In a case where gene amplification reaction is carried out in the reaction container 4 or a reaction container for gene amplification provided separately from the reaction container 4 of the reaction kit, the temperature control unit 83 is used to carry out temperature control for gene amplification reaction. Further, in a case where the reaction kit has an analysis section requiring temperature control, the temperature control unit 83 is used to carry out temperature control of the analysis section. The temperature control unit 83 may have both the function of carrying out temperature control for gene amplification reaction and the function of carrying out temperature control of the analysis section. The detection unit 38 shown in FIG. 20 generically denotes the detection means shown in FIGS. 7 to 9, 11, 13, and 14. The table 82 is moved in a forward-backward direction (X direction), and on the other hand, the detection unit 38 is supported so as to be able to move in a lateral direction (Y direction) orthogonal to the moving direction of the table 82. It is to be noted that the detection unit 38 may be fixed depending on a detection method used.

The drive unit 36 for driving the dispensation tip 20 is attached near the table 82 so as to be able to move in the Y and Z directions. As shown in FIG. 3, the drive unit 36 has a tip holding section 36*a* for holding the dispensation tip 20 by engaging with the proximal end of the dispensation tip 20 and a syringe drive section 36*b* for driving the syringe 22 by engaging with a plunger of the syringe 22 provided in the dispensation tip 20. The tip holding section 36*a* and the syringe drive section 36*b* are coaxially provided in the drive unit 36. Such a drive unit 36 allows both the movement of the dispensation tip 20 and the driving of the syringe 22 to be carried out.

Figure 25:
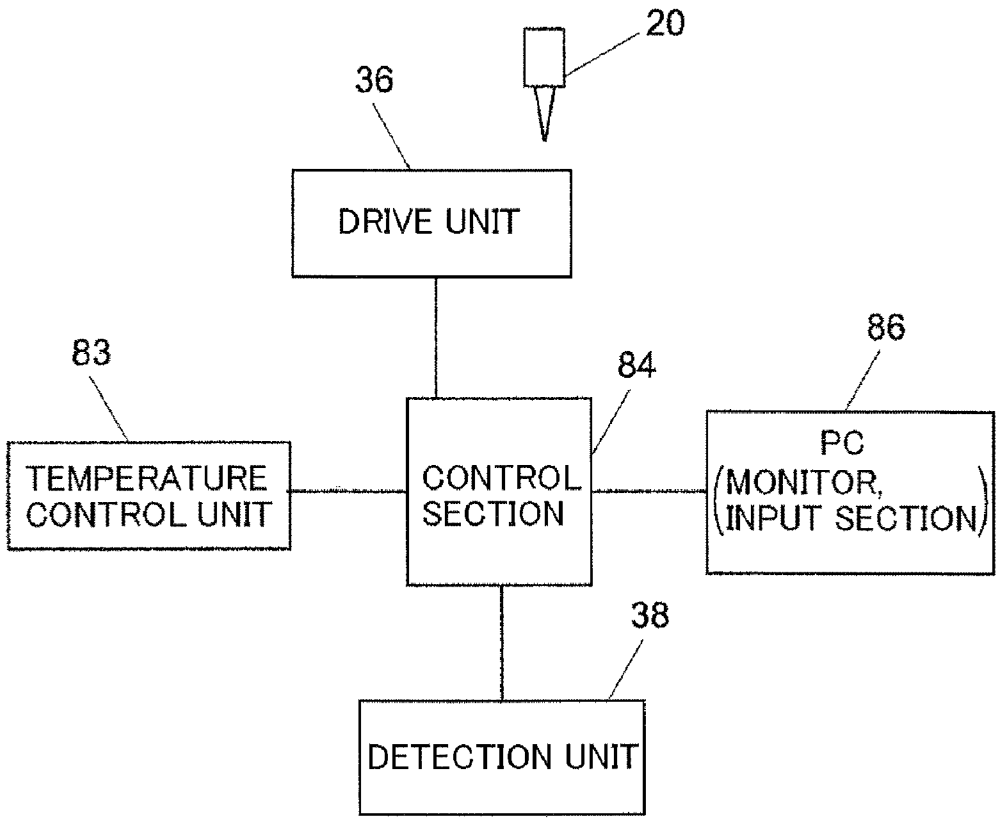
FIG. 25 is a block diagram showing the control system of the reaction kit treatment equipment shown in FIG. 20.

FIG. 25 is a block diagram showing the control system of the reaction kit treatment equipment. The reaction kit treatment equipment includes a control section 84 for controlling the treatment of the reaction kit 80 attached to the table 82. The control section 84 is constituted from a dedicated purpose computer (CPU) or a general-purpose personal computer. The control section 84 controls the movement of the dispensation tip 20 driven by the drive unit 36 engaged with the proximal end of the dispensation tip 20, dispensation operation by the dispensation tip 20, temperature control carried out by the temperature control unit 83, and the operation of the detection unit 38 for optically detecting a reaction product by irradiating the reaction container 4 of the reaction kit 80 with measuring light or excitation light.

In order to use the control section 84 as an input section externally operated or a monitor for displaying detection results, an external computer such as a personal computer (PC) 86 may be connected to the control section 84.

Industrial Applicability

The present invention can be applied to measurement of various chemical and biochemical reactions.

What is claimed is:

1. A reaction kit comprising:

a reaction plate having a reaction container for carrying out the reaction of a sample on the top surface side thereof;

a dispensation tip arranged above the top surface of the reaction plate;

a cover covering a space above the top surface of the reaction plate and movably supporting the dispensation tip so that a distal end thereof is located inside the space covered with the cover and a proximal end thereof is located outside the space; and a sample container provided in the space and configured separately from the reaction plate, wherein the dispensation tip is detachably attached to a drive unit externally provided and is driven to move between the sample container and the reaction container by the drive unit to carry out dispensation operation of the sample from the sample container to the reaction container, and the reaction plate, the dispensation tip, and the cover are kept in intimate contact with one another and are undetachably integrated together, keeping airtightness, and the reaction kit is disposable, wherein the cover has a cover main body and an upper cover, the cover main body having stiffness to maintain the shape of the cover and being provided integrally with the reaction plate, the upper cover being attached to the cover main body so as to be arranged above the top surface of the reaction plate, being formed of an airtight and flexible material, and holding and movably supporting the dispensation tip, and wherein the upper cover is formed of a bellows film or a flexibly deformable film, allowing the movement of the dispensation tip by flexibly deforming of the film.

2. The reaction kit according to claim 1, further comprising a sample introduction unit for introducing a sample into the sample container in the space covered with the cover from the outside through a sealable opening provided in a part of the cover.

3. The reaction kit according to claim 2, wherein the sample introduction unit further has a sealing member adhered to the cover so as to hermetically seal the opening after a sample is introduced into the space covered with the cover.

4. The reaction kit according to claim 3, wherein the cover main body has an opening, in which the sample introduction unit is arranged, and the sealing member is adhered to the cover main body.

5. The reaction kit according to claim 1, further comprising a sample introduction unit for introducing a sample into the sample container in the space covered with the cover from the outside through a sealable sample introduction port provided in a part of the cover, wherein the sample introduction port has an elastic member through which a sharp-tipped dispensation tool can pass to form a through hole closable by pulling out the dispensation tool due to its elasticity.

6. The reaction kit according to claim 5, wherein the sample introduction unit constitutes a container, the sample introduction port is provided in the side surface of the container and the container has an opening in the upper part thereof, and the container previously contains a sample pretreatment solution or a reagent.

7. The reaction kit according to claim 6, wherein the opening of the container is sealed with a cover film adhered thereto.

8. The reaction kit according to claim 5, wherein the sample introduction port can be hermetically sealed by adhering a sealing film thereto.

9. The reaction kit according to claim 1, wherein the reaction plate further has a reagent container provided on the top surface side thereof, which previously contains a reagent to be used for the reaction of the sample and is sealed with a film, wherein the dispensation tip is further driven to move between the reagent container and the reaction container by the drive unit to carry out dispensation operation of the reagent from the reagent container to the reaction container.

10. The reaction kit according to claim 1, wherein the dispensation tip has a syringe operated from the outside of the cover, and dispensation operation is carried out by operating the syringe.

11. The reaction kit according to claim 1, wherein the dispensation tip has a filter inside the tip portion thereof.

12. The reaction kit according to claim 1, wherein the reaction plate has a gene amplification unit provided on the top surface side thereof to carry out gene amplification reaction.

13. The reaction kit according to claim 1, wherein the reaction container is made of an optically-transparent material so that optical measurement can be carried out from the bottom side of the reaction container.

14. The reaction kit according to claim 1, wherein the reaction plate further has an analysis unit provided on the top surface side thereof to analyze a reaction product formed in the reaction container.

15. The reaction kit according to claim 14, wherein the analysis unit is an electrophoresis unit for analyzing a reaction product by electrophoretic separation.

16. The reaction kit according to claim 14, wherein when the reaction product has a gene, the analysis unit is a region where probes to be reacted with the gene are arranged.

17. The reaction kit according to claim 1, wherein at least an outer surface of a movable portion of the cover has been subjected to surface treatment to reduce a coefficient of friction.

18. The reaction kit according to claim 17, wherein the surface treatment is polyparaxylylene resin coating.

19. The reaction kit according to claim 17, wherein the surface treatment is fluorocarbon resin coating.

20. The reaction kit according to claim 17, wherein the flexible material is silicone rubber, ethylene propylene rubber, or butyl rubber.

* * * * *